United States Patent [19]

Sasho et al.

[11] Patent Number: 5,075,301

[45] Date of Patent: Dec. 24, 1991

[54] FURAN DERIVATIVES USEFUL FOR THE TREATMENT OF GASTRO-INTESTINAL DISORDERS

[75] Inventors: Setsuya Sasho; Shunji Ichikawa; Hiromasa Kato; Hiroyuki Obase; Katsuichi Shuto; Yoshimasa Oiji, all of Shizuoka, Japan

[73] Assignee: Kyowa Hakko Kogyo, Co., Ltd., Tokyo, Japan

[21] Appl. No.: 567,182

[22] Filed: Aug. 14, 1990

[30] Foreign Application Priority Data

Aug. 17, 1989 [JP] Japan ................... 1-211920

[51] Int. Cl.$^5$ .................. A61K 31/34; C07D 307/52

[52] U.S. Cl. ...................................... 514/211; 514/212; 514/218; 514/227.8; 514/231.5; 514/255; 514/326; 514/336; 514/385; 514/389; 514/392; 514/422; 514/471; 540/544; 540/575; 540/596; 544/60; 544/152; 544/379; 546/214; 546/283; 548/300; 548/305; 548/309; 548/318

[58] Field of Search ............... 549/487, 492, 493, 494, 549/495; 540/544, 575, 596; 544/60, 152, 379; 546/214, 283; 548/300, 305, 309, 318, 517; 514/211, 212, 218, 227.8, 231.5, 255, 326, 336, 385, 389, 392, 422, 471

[56] References Cited

U.S. PATENT DOCUMENTS 4,279,819 7/1981 Price et al. ................... 549/494

Primary Examiner—Bernard Dentz
Attorney, Agent, or Firm—Nixon & Vanderhye

[57] ABSTRACT

A furan derivative and a pharmaceutically acceptable salt thereof having gastrointestinal enterokinetic activity which is expected to be used in a broad spectrum of diseases associated with gastrointestinal dyskinesia.

7 Claims, No Drawings

FURAN DERIVATIVES USEFUL FOR THE TREATMENT OF GASTRO-INTESTINAL DISORDERS

FIELD OF THE INVENTION

The present invention relates to furan derivatives having gastroprokinetic activity.

BACKGROUND OF THE INVENTION

The motility of the gastrointestinal tract is controlled by the automatic nervous system, hormones, and the higher central nerves. It is known that an dysfunction of this control mechanism or an abnormality of the smooth muscle itself causes an anomalous movement of the gastrointestinal tract, thus causing such subjective and objective symptoms as nausea, vomiting, anorexia, dysphagia, abdominal distension, constipation and diarrhea. It is also known that administration of a drug acting on the gastrointestinal smooth muscle is an effective specific treatment of such symptoms and the efficacy of such a drug has been demonstrated clinically as well.

Representative drugs known to act on the smooth muscle include cholinergic drugs such as bethanechol, aclatonium, etc., cholinesterase inhibitors such as neostigmine, etc., dopamine antagonists such as metoclopramide, clebopride, domperidone, etc and drugs acting directly on smooth muscle such as trimebutine, etc., acetylcholine release-promoting drugs such as cisapride and so on.

A furan derivative structurally related to the compound of the invention is ranitidine which is a known antiulcer agent having histamine $H_2$-receptor blocking activity. This drug has also been reported to have activity to stimulate motility of the gastrointestinal tract [Scand. J. Gastroenterol., 21 (Suppl. 121), 30 (1986)] but its action is weak. It is also disclosed in U.S. Pat. Nos. 4,128,658, 4,169,855, 4,255,440 and 4,279,819 that ranitidine derivatives of the following formula (A) have antiulcer activity:

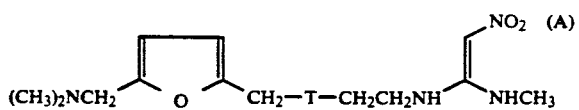

where T is $CH_2$, O or S.

Furan derivatives of the following formula (B), which have anti-$H_2$ histaminic activity, have been disclosed in U.S. Pat. Nos. 4,390,710 and 4,395,553, and EP-A-99122:

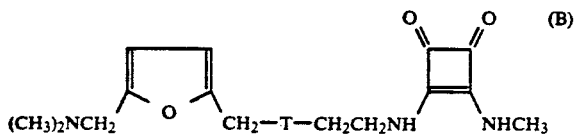

where T is as defined above.

U.S. Pat. No. 4,031,226 mentions that furancarboxamide derivatives of the following formula (C) have antiemetic activity:

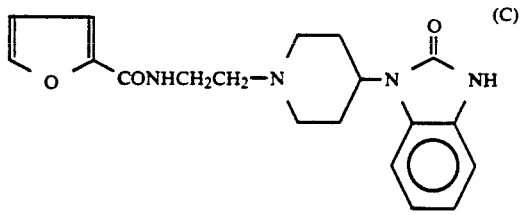

However, with the exception of ranitidine, none of these known compounds are described as ever having gastroprokinetic activity which the compounds of the invention have been demonstrated to have. Further, compounds conforming grossly to the above general formulas (A) and (B) where T is a nitrogen atom are novel compounds.

The above-mentioned cholinergic drugs and cholinesterase inhibitors have been found to cause hypotension and other side effects, while the dopamine antagonists are known to cause extrapyramidal symptoms, hyperprolactinemia and other side effects, and all of them are, thus, limited in utility.

There is a need for a drug which acts directly on the gastrointestinal smooth muscle devoid of adverse effects, a drug to be used safely with therapeutic efficacy in a broad spectrum of diseases associated with gastrointestinal dyskinesia.

SUMMARY OF THE INVENTION

The above need is fulfilled by the present invention which provides furan derivatives of the following general formula [hereinafter referred to as Compound (I), the same rule of abbreviation applies to other compounds hereinafter]:

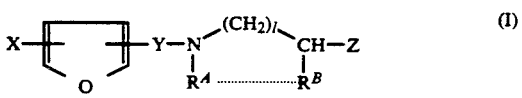

wherein X is hydrogen or $R^1CH_2$— where $R^1$ is lower alkoxy or $R^2R^3N$—, where $R^2$ and $R^3$ are the same or different and each is hydrogen or lower alkyl, or $R^2$ and $R^3$, taken together with the adjacent nitrogen atom, represent a heterocyclic group of the formula

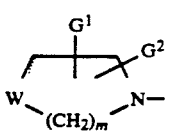

wherein ⸺ is a single bond or a double bond, and when ⸺ is a single bond, W represents —$CH_2$—, —O—, —S— or —$NR^4$—, where $R^4$ is hydrogen or lower alkyl, whereas when ⸺ is a double bond, W represents =CH—; $G^1$ and $G^2$ may be the same or different and each is hydrogen, lower alkyl, hydroxy or lower alkoxy; m is a whole number of 1 through 3;

Y is —$CH_2$— or

l is an integer of 1 through 3;

$R^A$ is hydrogen, lower alkyl, lower alkanoyl, or substituted or unsubstituted aroyl;

$R^B$ is hydrogen; or $R^A$ and $R^B$, taken together, represent —(CH$_2$)$_p$—, where p is 1 or 2;

Z is

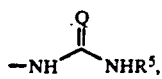

where Q is oxygen or sulfur, $R^5$ is hydrogen, lower alkyl, or substituted or unsubstituted aryl,

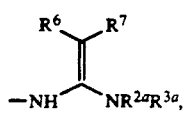

where $R^6$ and $R^7$ may be the same or different and each is hydrogen, cyano, lower alkoxycarbonyl, lower alkylsulfonyl, substituted or unsubstituted arylsulfonyl, or nitro; provided $R^6$ and $R^7$ cannot concurrently be hydrogen; $R^{2a}$ and $R^{3a}$ have the same meanings as R2 and R3 defined above,

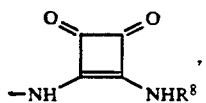

wherein $R^8$ is hydrogen or lower alkyl,

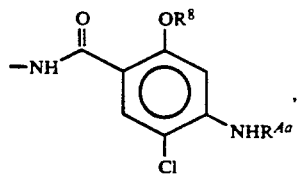

where $R^{Aa}$ has the same meaning as $R^A$ as defined above, $R^8$ is as defined above,

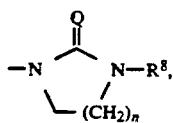

wherein n is 1 or 2; Q and $R^8$ are respectively as defined above,

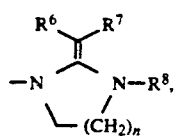

wherein $R^6$, $R^7$, $R^8$ and n are respectively as defined above,

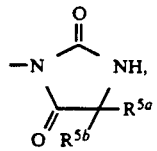

wherein $R^{5a}$ and $R^{5b}$ may be the same or different and each has the same meaning as $R^5$ defined above, or

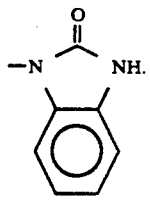

Phamaceutically acceptable salts of these compounds and pharmaceutical compositions containing them are also disclosed.

DETAILED DESCRIPTION OF THE INVENTION

In the above definitions of various groups in formula (I), lower alkyl and the alkyl moiety of the lower alkoxy, lower alkoxycarbonyl or lower alkylsulfonyl includes straight-chain or branched alkyl groups of 1 to 5 carbon atoms, such as methyl, ethyl propyl, isopropyl, butyl, isobutyl, sec-butyl, tert-butyl, pentyl and isopentyl. The lower alkanoyl includes straight-chain or branched alkanoyl groups of 1 to 5 carbon atoms, such as formyl, acetyl, propionyl, butyryl, isobutyryl, valeryl, pivaloyl and so on. The aryl and the aryl moiety of the aroyl or arylsulfonyl include phenyl and naphthyl, for instance, and as substituents thereof, there may be mentioned one or two members, which may be the same or different, of lower alkyl, lower alkoxy, halogen, nitro and so on. The lower alkyl or the alkyl moiety of the lower alkoxy mentioned just above has the same meaning as the aforementioned alkyl and the halogen means fluorine, chlorine, bromine or iodine.

The pharmaceutically acceptable salts of the compounds (I) include pharmaceutically acceptable acid addition salts, which may be inorganic acid salts such as hydrochloride, sulfate, phosphate, etc., or organic acid salts such as maleate, fumarate, citrate and so on.

The processes for production of compounds of the invention are described below.

Process 1

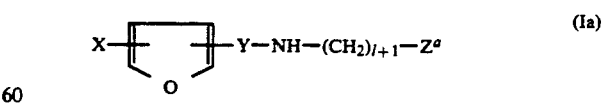

(Ia)

wherein $Z^a$ means

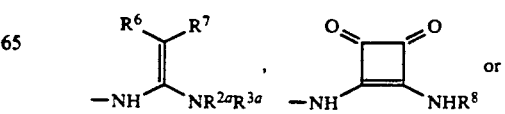

or

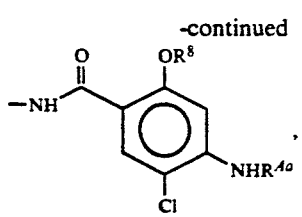

where $R^{2a}$, $R^{3a}$, $R^6$, $R^7$, $R^8$ and $R^{4a}$ are respectively as defined hereinbefore; X, Y and l are as defined hereinbefore.

Compound (Iaa) corresponding to the formula (Ia) wherein Y is —CO— can be produced by the following reaction steps.

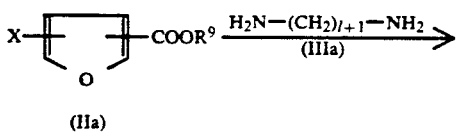

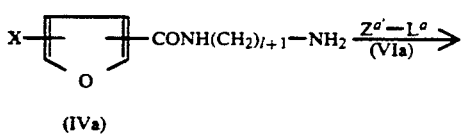

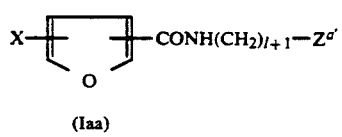

wherein $R^9$ is lower alkyl; $Z^{a'}$ means

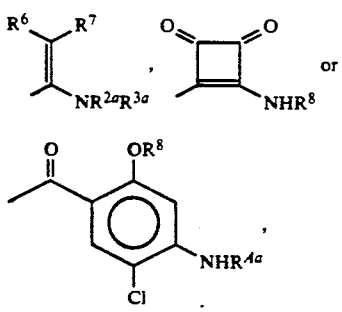

wherein $R^{2a}$, $R^{3a}$, $R^6$, $R^7$, $R^8$ and $R^{4a}$ are as defined hereinbefore, $L^a$ means a leaving group; X, $Z^a$ and l are as defined hereinbefore.

The leaving group $L^a$ means lower alkoxy, lower alkylthio or halogen, the lower alkyl moiety of the lower alkoxy or lower alkylthio and the lower alkyl $R^9$ have the same meaning as the alkyl mentioned previously, and the halogen is also as defined previously.

First, compound (IIa) is reacted with 10–20 equivalents of compound (IIIa) at 70°–100° C. for 5–12 hours to give compound (IVa).

This compound (IVa) is reacted with compound (IVa) in an inert solvent, such as an alcohol (e.g., methanol, ethanol, etc.), an amide (e.g. dimethylformamide etc.), or a halogenated hydrocarbon (e.g. methylene chloride, dichloroethane, etc.), or in the absence of a solvent, if necessary, in the presence of a base such as triethylamine or potassium carbonate at 0°–100° C. for 0.5–6 hours to give compound (Iaa). This reaction is preferably conducted under anhydrous conditions and, in the absence of a solvent, is preferably conducted under reduced pressure.

The compound (Iab) corresponding to compound (Ia) wherein Y—is —CH$_2$— can be synthesized by the following reaction steps.

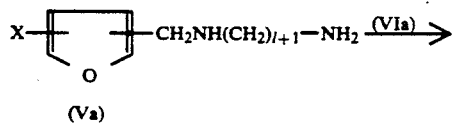

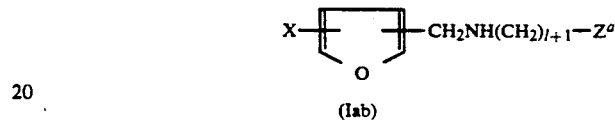

wherein X, $Z^a$ and l are respectively as defined hereinbefore.

The compound (Va) can be obtained by reducing the above-mentioned compound (IVa) with an appropriate reducing agent. This reaction can be conducted, for example, in an ether solvent such as tetrahydrofuran, diethyl ether or the like, in the presence of 1 to 2 equivalents of a reducing agent such as lithium aluminum hydride at a temperature between room temperature and the boiling point of the solvent for 5 to 20 hours.

Then, using compound (Va) and compound (VIa), compound (Iab) can be synthesized in the same manner as hereinbefore described.

Process 2

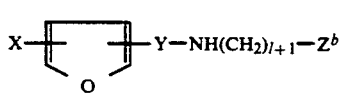

wherein $Z^b$ means

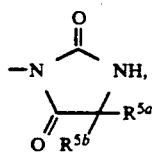

where $R^{5a}$ and $R^{5b}$ are as defined hereinbefore or

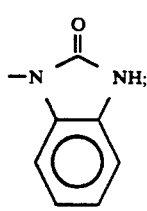

X, Y and l are respectively as defined hereinbefore.

The compound (Ib) can be synthesized by the following reactions steps.

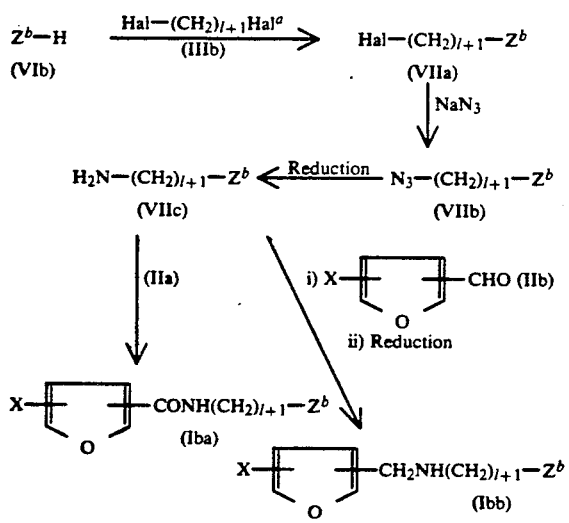

wherein Hal and Hal$^a$ are the same or different and each represents halogen; X, Z$^b$ and are respectively as defined hereinbefore.

Here, halogen means chlorine, bromine or iodine.

First, compound (VIb) is reacted with compound (IIIb) in an inert solvent in the presence of a base to give compound (VIIa). The base mentioned just above includes, among others, potassium hydroxide, potassium carbonate, sodium hydride and so on. The inert solvent includes tetrahydrofuran, dimethylformamide, methanol, ethanol, etc. and mixtures thereof. The reaction completes in 5 to 48 hours, when the reaction temperature is within the range of 0° C. to the boiling point of the solvent.

Then, this compound (VIIa) is reacted with 5 to 10 equivalents of sodium azide in an inert solvent such as dimethylformamide at 50°-70° C. for 1-10 hours to give compound (VIIb).

This compound (VIIb) is reduced to compound (VIIc) by an appropriate reduction reaction, for example, by treating (VIIb) in an inert solvent, such as lower alcohol (e.g. ethanol) or ethyl acetate, in the presence of a catalyst, e.g. palladium-carbon, in a hydrogen gas atmosphere at normal pressure at a temperature between room temperature and 50° C. for 6–12 hours.

Compound (Iba) corresponding to compound (Ib) wherein Y is —CO— can be synthesized from (VIIc) and (IIa) in the same manner as described in Process 1.

The compound (Ibb) wherein Y is —CH$_2$— can be synthesized by reacting compound (VIIc) with compound (IIb) in equimolar proportions in a lower alcohol, such as methanol, ethanol or the like, at a temperature between room temperature and 60° C., if necessary in the presence of a base, e.g. triethylamine, for 6–24 hours and, then, treating the reaction product with an appropriate reducing agent, such as sodium borohydride, at a temperature between 0° C. and room temperature for 1–6 hours.

Process 3

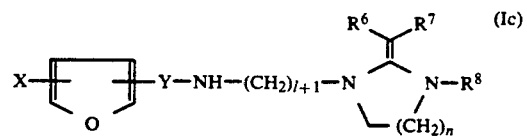

wherein X, Y, R$^6$, R$^7$, R$^8$, l and n are respectively as defined hereinbefore.

Compound (Ica) corresponding to compound (Ic) wherein Y is —CO— can be synthesized by the following reaction steps.

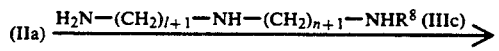

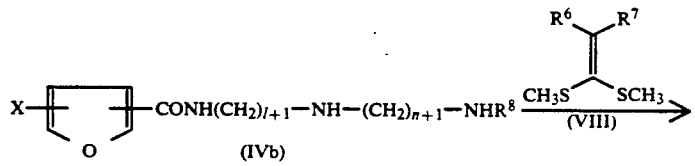

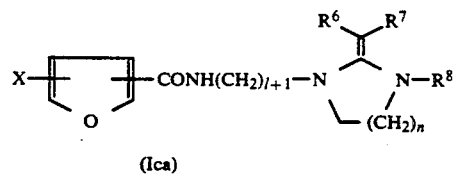

wherein X, R$^6$, R$^7$, R$^8$, and n are respectively as defined hereinbefore.

Thus compound (IIa) is reacted with 10 to 10 equivalents of compounds (IIIc) at 100°-150° C. for 6–24 hours to give compounds (IVb). Then, compounds (IVb) is reacted with compound (VIII) in the same manner as the process from compound (IVa) to compound (Iaa) described in Process 1 to give compound (Ica).

The compound (Ica) can also be synthesized by the following reaction steps.

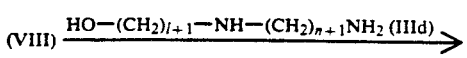

-continued

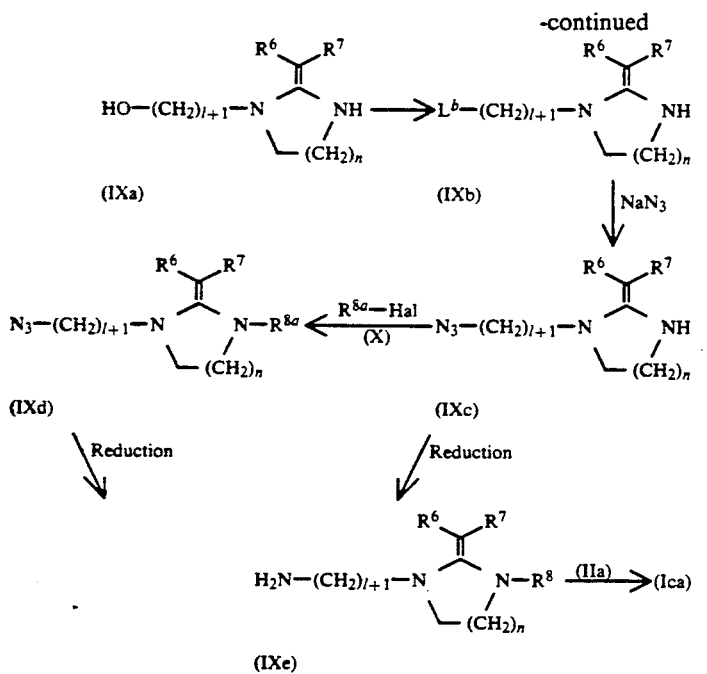

wherein $R^{8a}$ represents a lower alkyl group within the definition of $R^8$; $L^b$ means a leaving group; $R^6$, $R^7$, $R^8$, Hal, l and n are respectively as defined hereinbefore.

The leaving group $L^b$ means sulfonyloxy (e.g. p-toluenesulfonyloxy, methanesulfonyloxy, etc.) or halogen (e.g. chlorine, bromine and iodine).

This compound (VIII) is reacted with compound (IIId) in equimolar ratio at room temperature for 0.5–3 hours to give compound (IXa). This reaction is preferably conducted under reduced pressure.

The conversion from compound (IXa) to compound (IXb) can be carried out in the per se conventional manner. For example, in case $L^b$ is a sulfonyloxy group, this conversion can be achieved by reacting compound (IXa) with 1 to 3 equivalents of the corresponding sulfonyl halide in a basic solvent, such as pyridine, at a temperature between 0° C. and room temperature for 1–6 hours. In case $L^b$ means halogen, compound (IXb) can be obtained by reacting compound (IXa) with a halogenating agent such as thionyl chloride, phosphorus pentachlorice, phosphorus tribromide or the like.

The reaction process from compound (IXb) to compound (Ica) can be carried out in the same manner as described in Process 2.

When it is desired to obtain a compound of formula (Ica) wherein $R^8$ is a lower alkyl group, compound (IXc) is reacted with 1.5–2 equivalents of compound (X) in an inert solvent, such as dimethylformamide or dimethyl sulfoxide, in the presence of an appropriate base, such as sodium hydride, to give compound (IXd). Then, this compound (IXd) is treated in the same manner as described above to give compound (Ica).

Compound (Icb) corresponding to compound (Ic) wherein Y is —$CH_2$— can be synthesized by the following reaction steps.

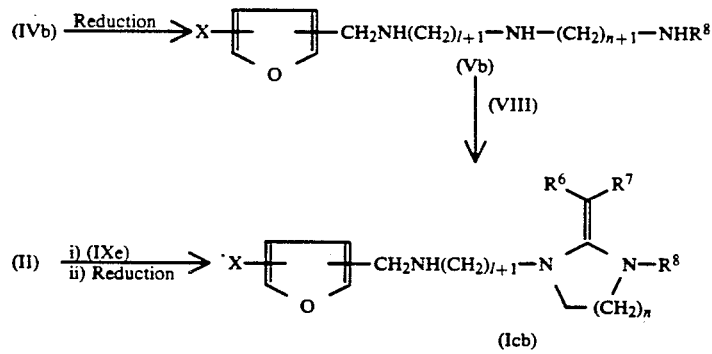

wherein X, $R^6$, $R^7$, $R^8$, l and n are respectively as defined hereinbefore.

Thus, compound (Icb) can be obtained by the steps of reducing compound (IVb) to compound (Vb) and reacting (Vb) with compound (VIII). This reaction can be conducted generally in the same manner as the conversion of compound (IVa) to compound (Iab) in Process 1.

Compound (Icb) can be synthesized from compound (IIb) and compound (IXe) in generally the same manner as the conversion of compound (VIIc) to compound (Ibb) in Process 2.

Process 4

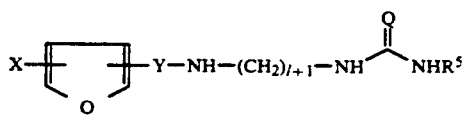

wherein X, Y, Q, $R^5$ and l are respectively as defined hereinbefore.

This compound (ID) can be synthesized by the following reaction steps.

−78° C. and room temperature to give compound (XIIa).

The subsequent steps starting with compound (XIIa) can be carried out in generally the same manner as the conversion of (IXa) to (Ica) or (Icb) in Process 3. In this manner, compound (Ida) or compound (Idb) can be obtained.

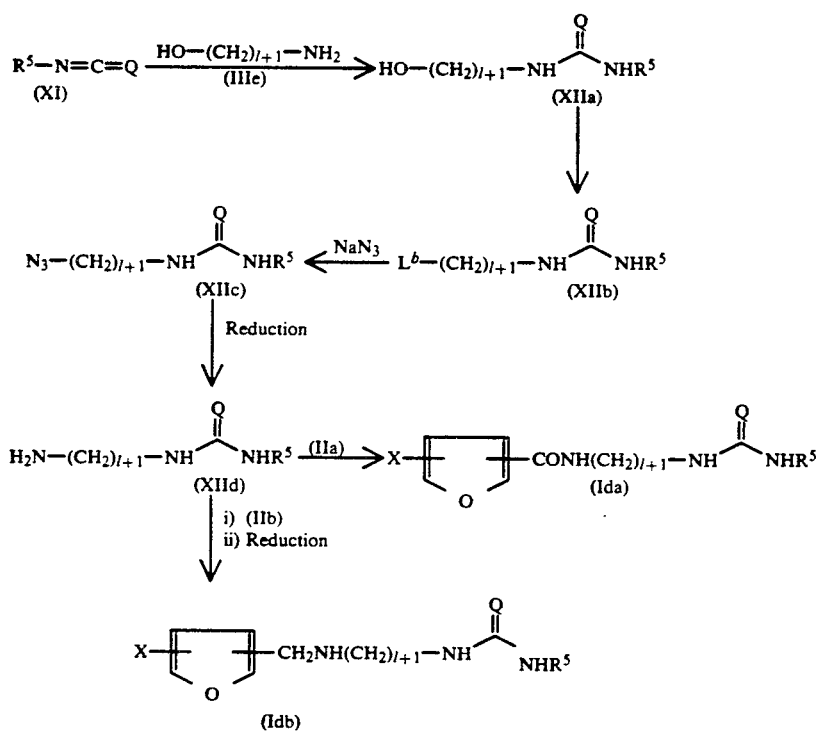

wherein X, Q, $R^5$, $L^b$ and l are respectively as defined hereinbefore.

Thus, compound (IIIe) and compound (XI) in equimolar amounts are reacted in an inert solvent such as an ether, e.g. tetrahydrofuran, or a halogenated hydrocarbon, e.g. methylene chloride, at a temperature between

Process 5

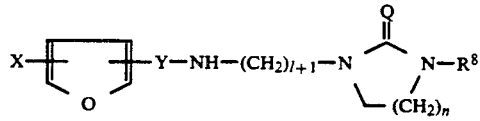

wherein X, Y, Q, $R^8$ and l are respectively as defined hereinbefore.

This compound (Ie) can be synthesized by the following reaction steps.

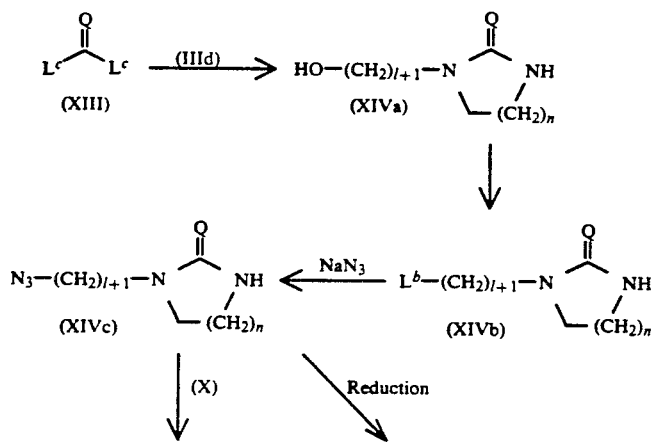

-continued

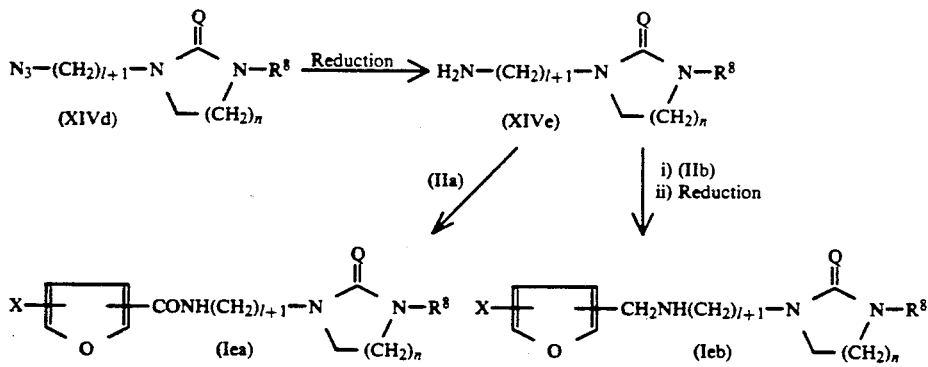

wherein L^c means a leaving group; X, Q, R^8, R^{8a}, L^b, l and n are respectively as defined hereinbefore.

Here, the leaving group L^c means halogen, such as chlorine or bromine, or imidazolyl, to name but a few. Compound (IIId) is then reacted with compound (XIII) in equimolar ratio in an inert solvent such as an ether, e.g. tetrahydrofuran, or an aromatic hydrocarbon, e.g. benzene or toluene, for 0.5–6 hours to give compound (XIVa).

The subsequent steps starting with compound (XIVa) can be carried out in generally the same manner as the conversion of (IXa) to (Ica) or (Icb) in Process 3 to thereby give compound (Iea) or (Ieb).

Process 6

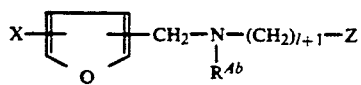

wherein R^{Ab} means a group other than hydrogen, within the definition of R^4; X, Z and l are respectively as defined hereinbefore.

Compound (Ifa) corresponding to compound (If) wherein R^{Ab} is a lower alkyl group can be synthesized by reacting compound (If') of the formula

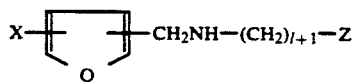

wherein X, Z and are respectively as defined hereinbefore with 3 to 5 equivalents of compound of the formula

R^{10}CHO    (XV)

wherein R^{10} is hydrogen or a lower alkyl group of 1 to 5 carbon atoms in an inert solvent, e.g. acetonitrile, in the presence of 1.5–2 equivalents of an appropriate reducing agent, e.g. sodium cyanoborohydride, at a temperature between 0° C. and room temperature for 1–2 hours.

Compound (Ifb) corresponding to compound (If) wherein R^{Ab} is lower alkanoyl or aroyl (hereinafter collectively referred to as acyl) can be obtained by reacting compound (If') with 1.5–2 equivalents of an appropriate acylating agent in a basic solvent, such as pyridine, at a temperature between 0° C. and room temperature for 1–12 hours. The acylating agent includes, among others, the acid anhydride and acid halide of the corresponding carboxylic acid.

Process 7

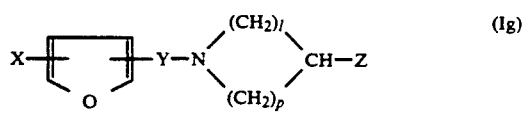

wherein X, Y, Z, l and p are respectively as defined hereinbefore.

Compound (Iga) corresponding to compound (Ig) wherein Y is —CO— can be synthesized by the following reaction.

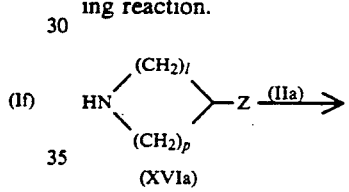

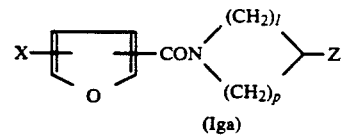

wherein X, Z, l and p are respectively as defined hereinbefore.

This reaction can be carried out in generally the same manner as the conversion of compound (IIa) to compound (IVa) in Process 1.

Compound (Igb) corresponding to compound (Ig) wherein Y is —CH_2— can be synthesized by the following reaction.

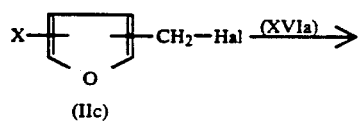

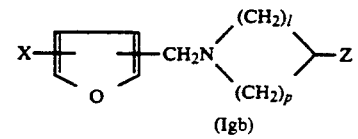

wherein X, Z, Hal, l and p are respectively as defined hereinbefore.

Thus, compound (IIc) is reacted with 2–3 equivalents of compound (XVIa) in an inert solvent, such as aromatic hydrocarbons (e.g. benzene, toluene, etc.), and amides (e.g. dimethylformamide) or a mixture of such solvents at room temperature for 10–48 hours to give compound (Igb).

Compound (Ig) can also be produced by the prior condensation of the furan ring to the nitrogen-containing heterocycle and subsequent modification of the side chain typically as described in Process 1 or 3. An example of this procedure is shown below.

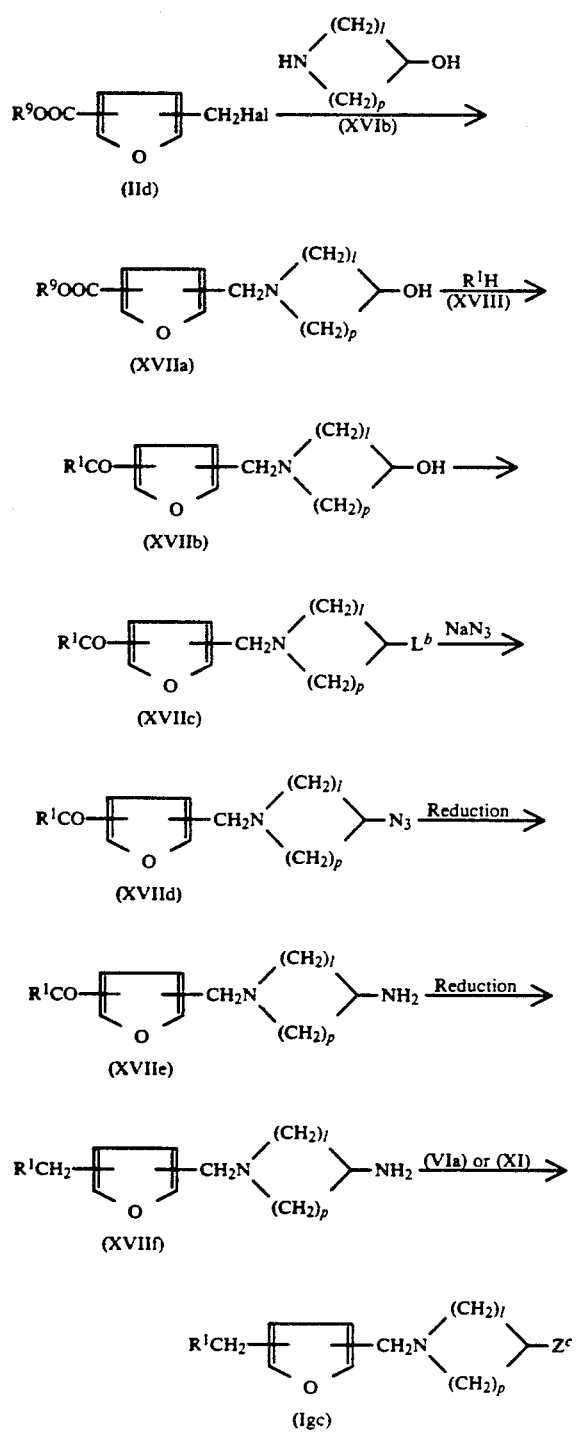

wherein $Z^c$ means $Z^a$ or

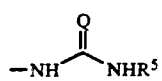

($Z^a$, Q and $R^5$ are respectively as defined hereinbefore); $R^1$, $R^9$, $L^b$, Hal, 1 and p are respectively as defined hereinbefore.

The process from compound (IId) to compound (XVIIa) can be carried out in generally the same manner as the process from compound (IIc) to compound (Igb) described hereinbefore.

Compound (XVIIa) is reacted with 5 to 20 equivalents of compound (XVIII) in an inert solvent, such as benzene, toluene, dimethylformamide, etc., or in the absence of a solvent, in the presence of 1 to 2 equivalents of an appropriate acid, preferably acetic acid, at a temperature between 80° C. and 150° C. for 6–48 hours to give compound (XVIIb).

The process from compound (XVIIb) to compound (XVIIe) can be carried out in generally the same manner as the process from compound (IXa) to compound (IXe) in Process 3.

The reduction of compound (XVIIe) to compound (XVIIf) can be carried out in generally the same manner as the conversion of compound (IVa) to compound (Va) in Process 1.

Production of compound (Igc) from compound (XVIIf) can be effected by generally the same procedure as that from compound (VIa) to compound (Iaa) in Process or that from compound (IIIe) to compound (XIIa) in Process 4.

The intermediate and end products obtained in the above-described processes can be isolated and purified by the purification procedures well known in organic synthetic chemistry, such as filtration, extraction, washing, drying, concentration, recrystallization and various chromatographic techniques. Each of the intermediate compounds may be directly submitted to the next reaction step without isolation.

When the desired product is a salt of compound (I) and the compound actually synthesized is such salt, it can be directly purified and recovered as a product. When the compound synthesized is a free compound, it can be converted to an optional salt by the per se known procedure.

The compound (I) and pharmaceutically acceptable salt may exist as adducts with water or other solvents. These adducts also fall within the scope of the invention.

Specific examples of compound (I) synthesized by the processes described hereinbefore are given in Table 1-1, Table 1-2 and Table 1-3.

TABLE 1-1
$$\text{X} \diagdown \!\!\!\! \diagdown \!\!\!\! \diagup \text{O} \diagdown \!\!\!\! \diagup \text{Y} - \overset{R^4}{\underset{|}{N}} - (CH_2)_l - CH_2 - Z$$
| Compound No. | X | Y | $R^4$ | l | Z |
|---|---|---|---|---|---|
| 1 | $(CH_3)_2NCH_2$ | $CH_2$ | H | 1 | 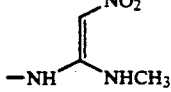 |
| 2 | " | " | " | " | 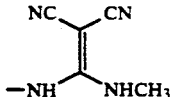 |
| 3 | " | " | " | " | 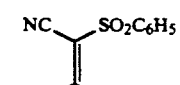 |
| 4 | " | " | " | " | 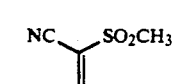 |
| 5 | H | " | " | " | 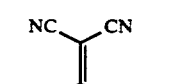 |
| 6 | $(CH_3)_2NCH_2$ | " | " | 2 | 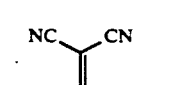 |
| 7 | " | CO | " | 1 | 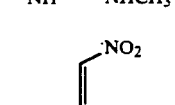 |
| 8 | H | CO | H | 1 | 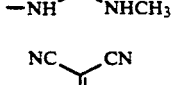 |
| 9 | $(CH_3)_2NCH_2$ | " | " | " | 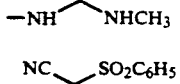 |
| 10 | " | " | " | " | 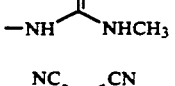 |
| 11 | $CH_3OCH_2$ | $CH_2$ | " | " | " |
| 12 | $[(CH_3)_2CH]_2NCH_2$ | " | " | " | " |
| 13 | 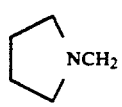 | " | " | " | " |
| 14 | 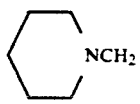 | " | " | " | " |

TABLE 1-1-continued

Structure: X—[furan ring, O]—Y—N(R^A)—(CH₂)ₗ—CH₂—Z

| Compound No. | X | Y | R^A | l | Z |
|---|---|---|---|---|---|
| 15 | " | " | " | " | $C_2H_5O_2C$, $CO_2C_2H_5$ on C=C with $-NH$ and $NHCH_3$ |
| 16 | $(CH_3)_2NCH_2$ | " | " | " | benzene ring with $OCH_3$, $-NHCO-$, $NH_2$, $Cl$ substituents |
| 17 | piperidinyl-$NCH_2$ | " | " | " | cyclobutenedione with $-NH$ and $NHCH_3$ |
| 18 | piperidinyl-$NCH_2$ | $CH_2$ | H | 1 | benzimidazolone ($-N$, $NH$, C=O) |
| 19 | " | " | " | " | imidazolidinedione ($-N$, $NH$, two C=O) |
| 20 | " | " | " | " | imidazolidinedione with $(CH_3)_2$ |
| 21 | " | " | " | " | imidazolidinedione with $(C_6H_5)_2$ |
| 22 | $(CH_3)_2NCH_2$ | " | " | " | $NC$, $CN$ on C=C with $-N$ and $NH$ (diazacycle) |
| 23 | " | " | " | " | $C_2H_5O_2C$, $CO_2C_2H_5$ on C=C with $-N$ and $NH$ (diazacycle) |
| 24 | $(CH_3)_2NCH_2$ | $CH_2$ | H | 1 | $NO_2$-CH= with $-N$ and $NH$ (diazacycle) |

TABLE 1-1-continued $$X \underset{O}{\underset{||}{\diagdown}} Y-\underset{R^4}{\underset{|}{N}}-(CH_2)_l-CH_2-Z$$

| Compound No. | X | Y | R⁴ | l | Z |
|---|---|---|---|---|---|
| 25 | CH₃\NCH₂ / C₂H₅ | " | " | " | NC\ /CN  =  −N  NH (imidazoline) |
| 26 | (C₂H₅)₂NCH₂ | " | " | " | " |
| 27 | ⟨pyrrolidine⟩NCH₂ | " | " | " | " |
| 28 | ⟨piperidine⟩NCH₂ | " | " | " | " |
| 29 | ⟨azepane⟩NCH₂ | " | " | " | " |
| 30 | 2-CH₃-piperidine-NCH₂ | " | " | " | " |
| 31 | 3-CH₃-piperidine-NCH₂ | " | " | " | " |
| 32 | 4-CH₃-piperidine-NCH₂ | CH₂ | H | 1 | NC\ /CN  =  −N  NH |
| 33 | 2,6-diCH₃-piperidine-NCH₂ | " | " | " | " |
| 34 | 3-CH₃O-piperidine-NCH₂ | " | " | " | " |
| 35 | 4-CH₃O-piperidine-NCH₂ | " | " | " | " |
| 36 | tetrahydropyridine-NCH₂ | " | " | " | " |

TABLE 1-1-continued $$X \underset{O}{\overset{}{\bigcirc}} Y - \underset{\underset{R^A}{|}}{N} - (CH_2)_l - CH_2 - Z$$

| Compound No. | X | Y | $R^A$ | l | Z |
|---|---|---|---|---|---|
| 37 | O-morpholine-NCH₂ | " | " | " | " |
| 38 | S-thiomorpholine-NCH₂ | " | " | " | " |
| 39 | CH₃N-piperazine-NCH₂ | " | " | " | " |
| 40 | H | CH₂ | H | 1 | NC\C=C/CN, -N...NH (imidazolidine) |
| 41 | HO-piperidine-NCH₂ (3-OH) | " | " | " | " |
| 42 | HO-piperidine-NCH₂ (4-OH) | " | " | " | " |
| 43 | piperidine-NCH₂ | " | " | " | NC\C=C/CN, -N...N-CH₃ |
| 44 | " | " | COCH₃ | " | NC\C=C/CN, -N...NH |
| 45 | " | " | CH₃ | " | " |

TABLE 1-2

$$X \underset{O}{\overset{}{\bigcirc}} Y - N \overset{2\ 3}{\underset{4}{\bigcirc}} Z$$

| Compound No. | X | Y | Z |
|---|---|---|---|
| 46 | piperidine-NCH₂ | CH₂ | 4-, NC\C=C/CN, -NH  NHCH₃ |

TABLE 1-2-continued

| Compound No. | X | Y | Z |
|---|---|---|---|
| 47 | " | " | 3-, NC\C=C/CN, -NH  NHCH₃ |

TABLE 1-3

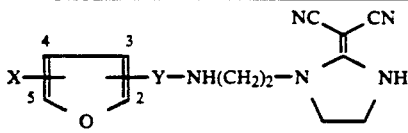

| Compound No. | Z | Y |
|---|---|---|
| 48 | 2-CH$_2$N-cyclohexyl | 3-CH$_2$ |
| 49 | 3-CH$_2$N-cyclohexyl | 2-CH$_2$ |
| 50 | 2-CH$_2$N-cyclohexyl | 4-CH$_2$ |
| 51 | 4-CH$_2$N-cyclohexyl | 2-CH$_2$ |

The following test data are intended to illustrate the pharmacological profile of compound (I).

TEST EXAMPLE 1

Acute toxicity test

Using male dd mice weighing 20±1 g in groups of 3, each test compound was orally administered (300 mg/kg, p.o.). After 7 days, the animals were observed for death and the minimum lethal dose (MLD) was calculated.

The results are shown in Table 2.

TEST EXAMPLE 2

Gastrointestinal motility stimulation test

From male Hartley guinea pigs weighing 250–400 g, ileal strips, 2–3 cm long, were isolated. The ileal strip was suspended in a Tyrode's solution bath (30 ml) while supplying a mixture gas of 95% $O_2$–5% $CO_2$ and maintained at 37±1° C. and using an isotonic transducer the longitudinal contractions of the strip were recorded. Supramaximal electric transmural stimulation of 1-millisecond duration was given at 10-second intervals.

Each test compound was dissolved or suspended in physiological saline and added into the organ bath. The effect of each test compound on electric transmural stimulation was calculated from the amplitude of contractions (A) before administration and the amplitude of contractions (B) after administration using the following equation.

$$\text{Amplification degree (\%)} = \frac{B - A}{A} \times 100$$

Some of the test compounds increased the tonus of ileum specimens and, thus, caused elevation of the baseline. For the compounds which caused this elevation, the result was shown as "baseline elevated"

The data are presented in Table 2.

TABLE 2

| Compound No. | Acute Toxicity (MLD) mg/kg, p.o. | Amplification Degree (%) (Electric Transmural Stimulation) (Concentration of Test Compound) | |
|---|---|---|---|
| | | $10^{-5}$ g/ml | $10^{-6}$ g/ml |
| 1 | >300 | 30.0 | |
| 2 | >300 | 80.5 | 31.0 |
| 6 | >300 | 34.0 | |
| 10 | >300 | 36.4 | 15.3 |
| 12 | >300 | 55.8 | 34.3 |
| 13 | >300 | 70.8 | 34.5 |
| 14 | >300 | 79.3 | 37.3 |
| 17 | >300 | 75.0 | 19.5 |
| 22 | >300 | baseline elevated | 56.0 |
| 25 | >300 | baseline elevated | 63.5 |
| 27 | >300 | baseline elevated | 12.0 |
| 28 | 100 | baseline elevated | baseline elevated |
| 29 | 200 | baseline elevated | 68.0 |
| 32 | >300 | baseline elevated | 52.0 |
| 34 | >300 | 81.3 | 23.0 |
| 38 | >300 | baseline elevated | 34.5 |
| 45 | >300 | 72.1 | 43.8 |
| Ranitidine (reference compound) | >300 | 42.2 | 35.0 |
| Metoclopramide (reference compound) | 200 | 33.4 | 18.0 |

It will be apparent from Table 2 that the compound (I) and pharmaceutically acceptable salt of the invention are low in toxicity and high in gastroprokinetic activity. Furthermore, these compounds do not show antihistaminic activity which is found in ranitidine and are excellent in isolation from undesirable actions such as gastric acid antisecretory action.

While the compound (I) or pharmaceutically acceptable salt can be administered as such, it is preferably provided as use-tailored pharmaceutical preparations. These pharmaceutical preparations can be advantageously used in human and animals.

The optimum route of administration will be selected in each therapeutic situation, from among oral, rectal, topical, intraoral, subcutaneous, intramuscular, intravenous and other routes.

The useful dosage forms include capsules, tablets, granules, powders, syrups, emulsions, suppositories and injections.

Liquid preparations suited for oral administration, such as emulsions and syrups, can be manufactured using such auxiliary materials as water, sugars such as sucrose, sorbitol, fructose, etc., glycols such as polyethylene glycol, propylene glycol, etc., oils such as sesame oil, olive oil, soybean oil, etc., preservatives such as p-hydroxybenzoic acid esters, etc., and flavors such as strawberry flavor, peppermint and so on. The capsules, tablets, powders, granules and the like can be manufactured by using appropriate excipients such as lactose, glucose, sucrose, mannitol, etc., disintegrating agents such as starch sodium alginate, etc., lubricating agents such as magnesium stearate, talc, etc., binding agents such as polyvinyl alcohol, hydroxypropylcellulose, gelatin, etc., surfactants such as fatty acid esters, plasticizers such as glycerin, etc., and so on.

Preparations particularly suited for parenteral administration are sterile aqueous products isotonic with the recipient's blood. Injections, for instance, can be manufactured using a vehicle which may be a sodium chloride solution, a glucose solution or a mixed solution of sodium chloride and glucose.

Preparations for topical application are prepared by dissolving or suspending the active compound in a medium or a mixture of media, such as mineral oil, petroleum oil, polyhydric alcohol and other vehicles which are generally used in preparations for topical application.

For rectal administration, the active compound can be formulated with a usual suppository base, such as cacao butter, hydrogenated fat, hydrogenated fat carboxylic acid, and so on.

In these non-oral preparations, too, there may be incorporated one or more auxiliary agents selected from among the diluents, flavors, preservatives (inclusive of antioxidants), excipients, disintegrators, lubricants, binders, surfactants and plasticizers mentioned for oral preparations.

The effective amount and the frequency of administration of the compound (I) or pharmaceutically acceptable salt of the invention depend on the dosage form, the patient's age and body weight, the type and severity of the disease to be treated and other clinical conditions. Generally speaking, however, the usual daily dosage is 0.01 to 1,000 mg/man, and the frequency of administration is once a day or a few divided doses a day.

The following Examples and Reference Examples are intended to illustrate the invention in further detail, but are not to be construed to limit the scope of the invention.

EXAMPLE 1

N-[2-[(5-Dimethylaminomethyl-2-furanyl)methylamino]ethyl]-N'-methyl-2-nitroethene-1,1-diamine (Compound 1)

A mixture consisting of 49.0 g (248 mmol) of ethyl 5-(dimethylaminomethyl)-2-furancarboxylate and 150 g (2.496 mol) of anhydrous ethylenediamine was heated at 80° C. for 2 hours. After cooling, the excess ethylenediamine was distilled off under reduced pressure to give 54.8 g (98.0%) of 5-(dimethylaminomethyl)-N-(2-aminoethyl)-2-furancarboxamide (Compound a) as light yellow oil.

NMR (CDCl$_3$) δ (ppm): 6.99 & 6.25 (1H, d, J=3.3 Hz), 6.90 (1H, bs), 3.49 (2H s), 3.49 (2H, t), 2.86 (2H, t), 2.25 (6H, s), 2.01 (2H, bs)

In 250ml of dry tetrahydrofuran was suspended 1.67 g (43.9 mmol) of lithium aluminum hydride and a solution of 5.0 g (22.2 mmol) of Compound a in 50 ml of dry tetrahydrofuran was added dropwise in a nitrogen stream at room temperature. After completion of dropwise addition, the mixture was heated under reflux for 12 hours. The reaction mixture was cooled with ice and, then, 3.4 ml of water, 1.7 ml of 20% aqueous sodium hydroxide solution and 8.5 ml of water were gradually added in that order. The mixture was then stirred under ice-cooling for 30 minutes. The insoluble matter was filtered off and the filtrate was concentrated under reduced pressure. Finally the residue was distilled under reduced pressure to recover 4.09 g (87.3%) of 5-(dimethylaminomethyl)-N-(2-aminoethyl)-2-furfurylamine (Compound b) as light yellow oil.

NMR (CDCl$_3$) δ (ppm): 6.31 (2H, s), 3.71 (2H, s), 3.64 (2H, s), 2.69 (4H, m), 2.25 (6H, s), 1.89 (3H, bs)

A mixture consisting of 1.29 g (6.55 mmol) of Compound b and 970 mg (6.55 mmol) of 1-methylthio-1-methylamino-2-nitroethylene was heated at 80° C. with constant aspiration for 2 hours. The resulting reaction mixture was subjected to silica gel column chromatography (chloroform-methanol 10:1→chloroform-methanol-triethylamine 100:10:1) to give 720 mg (37.1%) of Compound 1 as light tan-colored oil.

MS(m/z): 280 (M$^+$—OH)

NMR (CDCl$_3$) δ(ppm): 8.80 (1H, bs), 6.51 (1H s), 6.10 (2H, s), 6.08 (1H, bs), 3.75 (2H, s), 3.38 (2H, s), 3.27 (2H, m), 2.85 (5H, m), 2.36 (1H, bs), 2.23 (6H, s)

IR (KBr; cm$^{-1}$): 3400, 2960, 1650, 1570

In the following Examples 2 through 6, the respective compounds were synthesized generally in accordance with the procedure described in Example 1.

EXAMPLE 2

[[2-[(5-Dimethylaminomethyl-2-furanyl)methylamino]ethyl]amino(methylamino)methylene]propanedinitrile (Compound 2)

MS(m/z): 302 (M$^+$)

NMR (CDCl$_3$) δ (ppm): 8.81 (1H, bs), 6.10 (2H s), 5.80 (1H, bt), 3.80 (2H, s), 3.35 (2H, s), 3.25 (2H, q), 3.04 (3H, d), 2.84 (2H, m), 2.24 (6H, s), 1.79 (1H, bs)

IR (KBr; cm$^{-1}$): 3330 2950 2200 2160

EXAMPLE 3

N-[2-[(5-Dimethylaminomethyl-2-furanyl)methylamino]ethyl]-N'-methyl-2-benzenesulfonyl-2-cyano-1,1-diamine (Compound 3)

MS(m/z): 385(M$^+$)

NMR (CDCl$_3$) δ(ppm): 8.73 (1H, bs), 7.3–8.0 (5H m), 7.07 (1H, bs), 6.10 (2H, s), 3.68 (2H, s), 3.37 (2H, s) 3.17 (2H, m), 2.92 (3H, d), 2.75 (2H, m), 2.30 (6H, s)

IR (KBr: cm$^{-1}$): 3350, 2940, 2175

EXAMPLE 4

N-[2-[(5-Dimethylaminomethyl-2-furanyl)methylamino]ethyl]-N'-methyl-2-methanesulfonyl-2-cyano-1,1-diamine (Compound 4)

MS(m/s): 323 (M$^+$)

NMR (CDCl$_3$) δ (ppm): 8.75 (1H, bs), 6.97 (1H, bs), 6.10 (2H, s), 3.73 (2H, s), 3.38 (2H, s), 3.27 (2H, m), 3.04 (3H, s), 3.00 (3H, d), 2.80 (2H, m), 2.22 (6H, s)

IR (KRr; cm$^{-1}$): 3320, 2940, 2170

EXAMPLE 5

[[2-(2-Furanylmethylamino)ethyl]amino(methylamino)methylene]propanedinitrile (Compound 5)

m.p.: 100°–101° C.

Elemental analysis: C$_{12}$H$_{15}$N$_5$O Calcd. (%): C 58.95, H 6.17, N 28.77. Found (%): C 58.76, H 6.16, N 28.55.

MS(m/z): 245 (M$^+$)

NMR (CDCl$_3$) δ (ppm): 8.81 (1H, bs), 7.38 (1H, dd, J=0.73, 1.71 Hz), 6.34 (1H, dd, J=1.71, 3.17 Hz), 6.21 (1H, dd, J=0.73, 3.17 Hz), 5.80 (1h, bt), 3.80 (2H, s) 3.25 (2H, q), 3.04 (3H, d), 2.84 (2H, m), 1.79 (1H, bs)

IR (KBr; cm$^{-1}$): 3320–3480, 2200, 2160

EXAMPLE 6

[[3-[(5-Dimethylaminomethyl-2-furanyl)methylamino]propylamino](methylamino)methylene]propanedinitrile (Compound 6)

m.p.: 149°–151° C. (difumarate)

Elemental analysis: C$_{16}$H$_{24}$N$_6$O.2C$_4$H$_4$O$_4$ Calcd. (%): C 52.55, H 5.88, N 15.32. Found (%): C 52.79, H 5.90, N 15.04.

NMR (CDCl$_3$) δ (ppm): 8.21 (1H, bs), 6.03 (2H, s), 5.80 (1H, bt), 3.81 (2H, s), 3.33 (2H, s), 3.20 (2H, m), 3.05 (3H, d), 2.65 (2H, m), 2.24 (6H, s), 1.52 (2H, m)
IR (KBr; cm$^{-1}$): 3320, 2900–2950, 2200, 2160

EXAMPLE 7

5-(Dimethylaminomethyl)-N-[2-(1-methylamino-2-nitrovinylamino)ethyl]-2-furancarboxamide (Compound 7)

Using Compound a of Example 1 and 1-methylthio-1-methylamino-2-nitroethylene, the title compound was synthesized in otherwise the same manner as Example 1.
m.p.: 184°–186° C.
Elemental analysis: C$_{13}$H$_{21}$N$_5$O$_4$.1/5H$_2$O Calcd. (%): C 49.50, H 6.60, N 21.99 Found (%): C 49.58, H 6.85, N 22.24
MS(m/z): 294 (M$^+$—OH)
NMR (CDCl$_3$) δ (ppm): 8.77 (1H, bs), 6.95 & 6.40 (each 1H, each d, J=3.3 Hz), 6.58 (1H, bs), 3.42 (2H, s), 3.35 (4H, m), 2.83 (3H, d), 2.18 (6H, s)
IR (KBr; cm$^{-1}$): 3430, 3250, 1660

In the following Examples 8 through 10, the respective compounds were produced generally by the same procedure as Example 7.

EXAMPLE 8

N-[2-(1-Methylamino-2,2-dicyanovinylamino)ethyl]-2-furancarboxamide (Compound 8)
m.p.: 148°–149° C.
Elemental analysis: C$_{12}$H$_{13}$N$_5$O$_2$ Calcd. (%): C 55.59, H 5.05, N 27.01. Found (%): C 55.43, H 4.98, N 26.91
MS (m/z): 259 (M$^+$)
NMR (CDCl$_3$) δ (ppm): 7.52 (1H, d, J=1.83 Hz), 7.16 (1H, d, J=3.48 Hz), 6.96 (1H, m), 6.83 (1H, m), 6.55 (1H, dd, J=1.83, 3.48 Hz), 5.80 (1H, m), 3.68 (4H, bs), 3.01 (3H, d)
IR (KBr; cm-1): 3320-3480, 2220, 2160, 1645

EXAMPLE 9

5-(Dimethylaminomethyl)-N-[2(1-methylamino-2-benzenesulfonyl-2-cyanovinylamino)ethyl]-2-furancarboxamide (Compound 9)
MS (m/z): 399 (M+)
NMR (CDCl$_3$) δ (ppm): 7.37–8.08 (5H, m), 7.13–7.37 (3H, bs), 7.03 & 6.23 (each 1H, each d, J=3.2 Hz), 3.47 (2H, s), 3.40 (4H, m), 2.97 (3H, d), 2.23 (6H, s)
IR (KBr; cm$^{-1}$): 3330, 2175, 1640

EXAMPLE 10

5-(Dimethylaminomethyl)-N-[2-(1-methylamino-2,2-dicyanovinylamino)ethyl]-2-furancarboxamide (Compound 10)
m.p.: 136°–140° C.
Elemental analysis: C$_{15}$H$_{20}$N$_6$O$_2$ Calcd. (%): C 56.95, H 6.37, N 26.06. Found (%): C 56.69, H 6.37, N 25.84.
MS (m/z): 316 (M+)
NMR (DMSO-d$_6$) δ (ppm) 8.39 (1H, bq), 7.41 (1H, bs), 7.03 & 6.43 (each 1H, each d, J=3.3 Hz), 3.46 (2H, s), 3.38 (4H, m), 2.81 (3H, d), 2.16 (6H, s)
IR (KBr; cm$^{-1}$): 3320–3480, 2950–3010, 2220, 2160, 1650

EXAMPLE 11

[[2-[(5-Methoxyethyl-2-furanyl)methylamino]-ethyl]amino(methylamino)methylene]propanedinitrile (Compound 11)

In 20 ml of dry methanol was dissolved 5.0 g (26.5 mmol) of ethyl 5-chloromethyl-2-furancarboxylate, followed by addition of 20 ml of a 28% solution of sodium methoxide in methanol. The mixture was stirred at room temperature for 17 hours, at the end of which time it was neutralized with 1N-hydrochloric acid. The resulting precipitate was filtered off and the filtrate was concentrated under reduced pressure. The residue was dissolved in chloroform and the solution was washed with a saturated aqueous sodium chloride solution and dried over anhydrous magnesium sulfate. The solvent was then distilled off under reduced pressure to give 3.73 g (82.7%) of methyl 5-methoxymethyl-2-furancarboxylate (Compound c) as light yellow oil.
NMR (CDCl$_3$) δ (ppm): 7.13 & 6.45 (each 1H, each d, J=3.4 Hz), 4.43 (2H, s), 3.84 (3H, s), 3.36 (3H, s)

Using Compound c and anhydrous ethylenediamine, the corresponding procedure of Example 1 was repeated to give 5-(methoxymethyl)-N-(2-aminoethyl)-2-furancarboxamide (Compound d) as light yellow oil.
NMR (CDCl$_3$) δ (ppm): 8.09 (1H, bs), 7.09 & 6.41 (each 1H, each d, J=3.4 Hz), 4.38 (2H, s), 3.47 (2H, t), 3.36 (3H, s), 2.88 (2H, t), 2.11 (2H, bs)

Compound d was reduced in the same manner as Example 1 to give 5-(methoxymethyl)-N-(2-aminoethyl)furfurylamine (Compound e) as light yellow oil.
NMR (CDCl$_3$) δ (ppm): 6.21 & 6.09 (each 1H, each d, J=3.3 Hz)), 4.31 (2H, s), 3.73 (2H, s), 3.30 (3H, s), 2.66 (4H, m), 1.76 (3H, bs)

Using Compound e and [(methylthio)(methylamino)methylene]malononitrile, the corresponding procedure of Example 1 was repeated to give Compound 11 as light yellow foam.
m.p.: 135°–136° C. (hemifumarate)
Elemental analysis: C$_{14}$H$_{19}$N$_5$O.½C$_4$H$_4$O$_4$. 1/5 H$_2$O Calcd. (%): C 57.37, H 6.44, N 20.91 Found (%): C 57.16, H 6.41, N 20.79
MS (m/z) 289 (M+), 257 (M+—CH$_3$OH)
NMR (DMSO-d$_6$+CD$_3$OD) δ (ppm): 6.58 (1H, s), 6.36 & 6.27 (each 1H, each d, J=3.11 Hz), 4.30 (2H, s), 3.75 (2H, s), 3.25 (2H, t), 3.22 (3H, s), 2.85 (3H, s), 2.72 (2H, t)
IR (KBr; cm$^{-1}$): 2950, 2200, 2160, 1190, 1060

EXAMPLE 12

[[2-[(5-Diisopropylaminomethyl-2-furanyl)methylamino]ethyl]amino(methylamino)methylene]-propanedinitrile (Compound 12)

In 10 ml of toluene was dissolved 3.0 g (15.9 mmol) of ethyl 5-chloromethyl-2-furancarboxylate, followed by addition of 10 ml (71.5 mmol) of diisopropylamine. The mixture was heated at 100° C. for 48 hours. After cooling, the reaction mixture was filtered to remove the precipitate and the filtrate was concentrated under reduced pressure. The residue was then purified by silica gel column chromatography (chloroform-methanol =20:1) to give 2.26 g (56.1%) of ethyl 5-diisopropylaminomethyl-2-furancarboxylate (Compound f) as light tan-colored oil.
NMR (CDCl$_3$) δ (ppm): 7.06 & 6.28 (each 1H, each d, J=3.2 Hz), 4.31 (2H, q), 3.68 (2H, s), 3.05 (2H, m), 1.35 (3H, t), 1.04 (12H, d)

Using Compound f and anhydrous ethylenediamine, the corresponding procedure of Example 1 was followed to give 5-(diisopropylaminomethyl)-N-(2-aminoethyl)-2-furancarboxamide as tan-colored oil. Reduction of this compound in the same manner as Example 1 without prior purification gave 5-(diisopropylaminomethyl)-N-(2-aminoethyl)furfurylamine (Compound g) as light yellow oil.

NMR (CDCl₃) δ (ppm): 6.07 (2H, s), 3.75 (2H, s), 3.62 (2H, s), 3.06 (2H, m), 2.70 (4H, m), 1.92 (3H, bs), 1.06 (12H, d)

Using Compound g and [(methylthio)(methylamino)methylene]propanedinitrile, the corresponding procedure of Example 1 was followed to give Compound 12 as light yellow crystals.

m.p.: 79°–80° C.

Elemental analysis: $C_{19}H_{30}N_6O$ Calcd. (%): C 63.66, H 8.44, N 23.44. Found (%): C 63.81, H 8.49, N 23.55.

MS (m/z): 358 (M+), 343 (M+—CH3), 315 [M+—(CH₃)₂CH]

NMR (CDCl₃) δ (ppm): 9.0 (1H, bs), 6.10 (2H, s), 5.84 (1H, bt), 3.74 (2H, s), 3.60 (2H, s), 3.25 (2H, m), 3.06 (2H, m), 3.05 (3H, d), 2.82 (2H, m), 1.97 (1H, bs), 1.06 (12H, d)

IR (KBr; cm⁻¹): 3220, 2900–2950, 2200, 2160

In the following Examples 13 through 15, the respective compounds were produced in accordance with the procedure set forth in Example 12.

EXAMPLE 13

[[2-[(5-Pyrrolidinylmethyl-2-furanyl)methylamino]ethyl](methylamino)methylene]propanedinitrile (Compound 13)

m.p.: 103°–104° C.

Elemental analysis: $C_{17}H_{24}N_6O$ Calcd. (%): C 62.17, H 7.37, N 25.59. Found (%): C 62.20, H 7.40, N 25.301.

MS (m/z):328 (M+)

NMR (CDCl₃) δ (ppm): 8.57 (1H, bs), 6.12 (2H, s), 3.76 (2H, s), 3.59 (2H, s), 3.26 (2H, bq), 3.04 (3H, d), 2.81 (2H, t), 2.52 (4H, m), 1.79 (4H, m)

IR (KBr; cm⁻¹): 3300, 2900–2950, 2200, 2160

EXAMPLE 14

[[2-[(5-Piperidinomethyl-2-furanyl)methylamino]ethyl](methylamino)methylene]propanedinitrile (Compound 14)

Elemental analysis: $C_{18}H_{26}N_6O \cdot 2HCl \cdot H_2O$ Calcd. (%): C 49.89, H 6.98, N 19.39. Found (%): C 49.60, H 6.89, N 19.09.

MS (m/z): 342 (M+)

NMR (CDCl₃) δ (ppm): 8.60 (1H, bs), 6.12 (2H, s), 3.75 (2H, s), 3.60 (2H, s), 3.25 (2H, bq), 3.04 (3H, d), 2.82 (2H, t), 2.41 (4H, m), 1.60 (6H, m)

IR (KBr; cm⁻¹): 3200, 2900–2960, 2200, 2160

EXAMPLE 15

Diethyl [[2-[(5-piperidinomethyl-2-furanyl)methylamino]ethyl]amino(methylamino)methylene]malonate (Compound 15)

Elemental analysis: $C_{22}H_{36}N_4O_5 \cdot 1/2H_2O$ Calcd. (%): C 59.30, H 8.37, N 12.57. Found (%): C 59.31, H 8.39, N 11.90.

MS (m/z): 437 (M+1)

NMR (CDCl₃) δ (ppm): 9.34 (1H, bs), 9.19 (1H, bs), 6.14 & 6.11 (each 1H, each d, J=3.11 Hz), 4.14 (4H, q), 3.77 (2H, s), 3.52 (2H, s), 3.29 (2H, t), 2.92 (3H, d), 2.82 (2H, t), 2.44 (4H, m), 1.80 (1H, bs), 1.50 (6H, m), 1.28 (6H, t)

IR (KBr; cm-1): 3400, 2950, 1740, 1200

EXAMPLE 16

N-[2-[(5-Dimethylaminomethyl-2-furanyl)methylamino]ethyl]-2-methoxy-4-amino-5-chlorobenzamide (Compound 16)

In 60 ml of dry tetrahydrofuran was suspended 1.5 g (6.2 mmol) of 2-methoxy-4-acetamide-5-chlorobenzoic acid, followed by addition of 622 mg (6.2 mmol) of triethylamine. To this mixture was added a solution of 668 mg (6.2 mmol) of ethyl chloroformate in 5 ml of dry tetrahydrofuran dropwise at −10° C. and the mixture was stirred for one hour. Then, a solution of 1.21 g (6.2 mmol) of 5-(dimethylaminomethyl)-N-(2-aminoethyl)-furfurylamine in 10 ml of dry tetrahydrofuran was added dropwise and the mixture was stirred at −10° C. for 1 hour and, then, allowed to stand at room temperature overnight. The reaction mixture was filtered and the filtrate was concentrated under reduced pressure. The residue was dissolved in 60 ml of methanol, and after addition of 8.5 g (61.6 mmol) of potassium carbonate, the solution was heated under reflux for 2 hours. The reaction mixture was filtered, the filtrate was concentrated under reduced pressure and the residue was subjected to silica gel column chromatography (ethyl acetate-methanol-triethylamine=60:4:1) to give 614 mg (26.2%) of Compound 16 as yellow crystals.

m.p.: 91°–93° C.

Elemental analysis: $C_{18}H_{25}ClN_4O_3 \cdot \frac{1}{2}H_2O$ Calcd. (%): C 55.45, H 6.72, N 14.37. Found (%): C 55.58, H 6.65, N 14.38.

MS (m/z): 383 (M++3), 381 (M++1)

NMR (CDCl₃) δ (ppm): 8.09 (1H, s), 8.05 (1H, bt), 6.28 (1H, s), 6.11 (2H, s), 4.40 (1H, s), 3.87 (3H, s), 3.80 (2H, s), 3.52 (2H, dt), 3.43 (2H, s), 2.83 (2H, t), 2.25 (6H, s), 2.22 (1H, bs)

IR (KBr; cm⁻¹): 3350, 2760–2950, 1630

EXAMPLE 17

1-Methylamino-2-[[2-[(5-piperidinomethyl-2-furanyl)methylamino]ethyl]amino]cyclobutene-3,4-dione (Compound 17)

A mixture consisting of 2.81 g (11.86 mmol) of (5-piperidinomethyl)-N-(2-aminoethyl)furfurylamine and 1.84 g (11.86 mmol) of 1-methylamino-2-ethoxycyclobutene-3,4-dione was heated at 80° C. for 1 hour. The reaction mixture was subjected to silica gel column chromatography (chloroform-methanol-triethylamine=100:10:1) and the resulting crude crystals were recrystallized from acetone to give 1.23 g (30.0%) of Compound 17 as white crystals.

m.p.: 145°–147° C.

Elemental analysis: $C_{18}H_{26}N_4O_3 \cdot 2/5H_2O$ Calcd. (%): C 61.20, H 7.53, N 15.86. Found (%): C 61.36, H 7.53, N 15.69.

MS (m/z): 351 (M+)

NMR (CDCl₃) δ (ppm): 7.46 (2H, bs), 6.07 (2H, s), 3.76 (2H, s), 3.68 (2H, m), 3.44 (2H, s), 3.29 (3H, d), 2.84 (2H, t), 2.36 (4H, m), 2.30 (1H, bs) 1.50 (6H, m))

IR (KBr; cm⁻¹): 3200, 2900–2950, 1790

EXAMPLE 18

N-[2-[(5-Piperidinomethyl-2-furanyl)methylamino]ethyl]-2,3-dihydro-2-oxo-1H-benzimidazole (Compound 18)

To a solution of 5.0 g (37.3 mmol) of 2,3-dihydro-2-oxo-1H-benzimidazole in 100 ml of dimethylformamide was added 1.5 g (37.5 mmol) of 60% sodium hydride under ice-cooling. This reaction mixture was stirred at room temperature for 1 hour, at the end of which time 27.0 g (186.6 mmol) of 1-bromo-2-chloroethane was added. The mixture was then heated at 100° C. for 20 hours. After cooling, the reaction mixture was filtered and the filtrate was concentrated under reduced pressure. To the residue was added 200 ml of ethyl acetate, the insolubles were filtered off and the filtrate was washed with 3 portions of saturated aqueous sodium chloride solution. The organic layer was dried over anhydrous magnesium sulfate and the solvent was distilled off. The residue was purified by silica gel column chromatography (chloroform-methanol=30:1) to give 1.59 g (19.5%) of a 1:1 (approx.) mixture of 1-(2-chloroethyl)-2,3-dihydro-2-oxo-1H-benzimidazole (Compound h) and 1-(2-bromoethyl)-2,3-dihydro-2-oxo-1H-benzimidazole (Compound h') as white crystals.

MS (m/z):242 (M+2), 240 (M+), 198 (M++2), 196 (M+)

In 30 ml of dimethylformamide were dissolved 1.5 g of the above 1:1 (approx.) mixture of Compound h and Compound h', 1.5 g (9.9 mmol) of sodium iodide and 5.0 g (76.3 mmol) of sodium azide and the solution was heated at 120° C. for 48 hours. After cooling, the solvent was distilled off and 50 ml of ethyl acetate was added to the residue. The insolubles were filtered off and the filtrate was washed twice with 5% aqueous sodium thiosulfate solution and, then, three times with saturated aqueous sodium chloride solution. The organic layer was dried over anhydrous magnesium sulfate and the solvent was distilled off under reduced pressure to give 1.38 g (98.9%) of 1-(2-azidoethyl)-2,3-dihydro-2-oxo-1H-benzimidazole (Compound i) as light yellow crystals.

MS (m/z): 203 (M+)

In 150 ml of ethanol was dissolved 1.3 g (6.4 mmol) of Compound i followed by addition of a suspension of 65 mg (5 w/w%) of 10% palladium-carbon in 2 ml of water. The mixture was stirred at room temperature for 4.5 hours, with hydrogen gas being bubbled into the mixture. The reaction mixture was then filtered and the filtrate was concentrated to give 1.01 g (89.1%) of 1-(2-aminoethyl)-2,3-dihydro-2-oxo-1H-benzimidazole (Compound j) as white crystals.

NMR (CDCl$_3$) δ (ppm): 7.0 (5H, m), 3.94 (2H, t, J=6.7 Hz), 3.07 (2H, t, J=6.7 Hz), 2.8–4.3 (2H, bs)

In 100 ml of dry ethanol were dissolved 1.2 g (6.78 mmol) of Compound j and 1.3 g (6.78 mmol) of 5-piperidinomethylfurfural and the solution was stirred at room temperature for 20 hours. The reaction mixture was then cooled with ice and 1.18 g (31.1 mmol) of sodium borohydride was gradually added. The mixture was further stirred under ice-cooling for 1.5 hours. The reaction mixture was then concentrated, and after addition of methylene chloride, the resulting solution was washed with 2 portions of saturated aqueous sodium chloride solution. The organic layer was dried over anhydrous magnesium sulfate and the solvent was distilled off. Finally the residue was purified by silica gel column chromatography (chloroform-methanol=10:1→chloroform-methanol-triethylamine=100:10:1) to give 1.26 g (52.9%) of Compound 18 as light yellow oil.

m.p.: 83°–85° C. (foaming) (difumarate)

Elemental analysis: C$_{20}$H$_{26}$N$_4$O$_2$.2C$_4$H$_4$O$_4$.2/5 H$_2$O
Calcd. (%): C 56.64, H 5.91, N 9.44. Found (%): C 56.85, H 5.70, N 9.13.

MS (m/z): 354 (M+)

NMR (CDCl$_3$) δ (ppm): 7.69 (5H, m), 6.05 (2H, s), 3.98 (2H, bt), 3.74 (2H, s) 3.43 (2H, s), 2.98 (2H, m), 2.41 (4H, m), 1.51 (7H, m)

IR (KBr; cm$^{-1}$): 3050, 1710

EXAMPLE 19

3-[2-[(5-Piperidinomethyl-2-furanyl)methylamino]ethyl]imidazolidine-2,4-dione (Compound 19)

In a mixture of 3.3 g (50 mmol) of 85.5% potassium hydroxide, 200 ml of dimethylformamide and 100 ml of ethanol was dissolved 5.0 g (50 mmol) of hydrantoin followed by addition of 35.9 g (250 mmol) of 1-bromo-2-chloroethane. This mixture was heated under reflux for 24 hours and the solvent was distilled off under reduced pressure. To the residue was added 300 ml of chloroform and the insolubles were filtered off. The filtrate was washed with 2 portions of saturated aqueous sodium chloride solution and the washings were combined and extracted with 200 ml of chloroform. The organic layers were combined and dried over anhydrous magnesium sulfate and the solvent was distilled off. Finally the residue was purified by silica gel column chromatography (chloroform-methanol=30:1) to give 4.5 g (55.4%) of 3-(2-chloroethyl)imidazolidine-2,4-dione (Compound k) as white crystals.

MS (m/z): 164 (M++2), 162 (M+)

In Example 19, the procedure of Example 18 was repeated except that Compound k was used in lieu of Compound h to give Compound 19 as light yellow oil.

m.p.: 133°–136° C. (difumarate)

Elemental analysis: C$_{16}$H$_{24}$N$_4$O$_3$.2C$_4$H$_4$O$_6$.H$_2$O
Calcd. (%): C 50.21, H 6.04, N 9.76. Found (%): C 50.24, H 6.19, N 9.51.

MS (m/Z): 320 (M+)

NMR (DMSO-d$_6$) δ (ppm): 8.04 (1H, bs), 6.58 (4H, s), 6.30 (2H, s), 3.87 (2H, s), 3.84 (2H, s), 3.63 (2H, s), 3.51 & 2.79 (each 2H, each t, J=6.41 Hz), 2.51 (4H, m), 1.53 (4H, m), 1.39 (2H, m)

IR (KBr; cm$^{-1}$): 3400, 2950, 1700

In the following Examples 20 and 21, the respective compounds were produced in accordance with the procedure set forth in Example 19.

EXAMPLE 20

3-[2-[(5-Piperidinomethyl-2-furanyl)methylamino]ethyl]-5,5-dimethylimidazolidine-2,4-dione (Compound 20)

MS (m/z): 348 (M+)

NMR (CDCl$_3$) δ (ppm): 6.57 (1H, bs), 6.05 (2H, s), 3.74 (2H, s), 3.59 & 2.84 (each 2H, each t, J=6.6 Hz), 3.45 (2H, s), 2.41 (4H, m), 1.50 (6H, m), 1.43 (6H, s)

IR (KBr; cm$^{-1}$): 3400, 2950, 1690

EXAMPLE 21

3-[2[(5-Piperidinomethyl-2-furanyl)methylamino]ethyl]-5,5-diphenylimidazolidine-2,4-dione (Compound 21)

m.p.; 158°–160.5° C. (difumarate)

Elemental analysis: C$_{28}$H$_{32}$N$_4$O$_3$.2C$_4$H$_4$O$_4$.1/5H$_2$O
Calcd. (%): C 61.04, H 5.75, N 7.91. Found (%): C 61.30, H 5.60, N 7.65.

MS (m/z): 472 (M+)

NMR (CDCl$_3$) δ (ppm): 7.32 (10H, m), 6.97 (1H, bs), 6.02 & 5.98 (each 1H, each d, J=3.12 Hz), 3.73 (2H,s), 3.64 (2H, t, J=6.7 Hz), 3.37 (2H, s), 2.87 (2H, t, J=6.7 Hz), 2.36 (4H, m), 1.57 (6H, m)

IR (KBr; m$^{-1}$) 3400, 2950, 1700

EXAMPLE 22

[1-[2-[(5-Dimethylaminomethyl-2-furanyl)methylamino]ethyl]-2-imidazolidinylidene]propanedinitrile (Compound 22)

A mixture consisting of 20.0 g (101.5 mmol) of ethyl 5-(dimethylaminomethyl)-2-furancarboxylate and 52.3 g (507.8 mmol) of diethylenetriamine was heated at 80° C. for 5 hours. The excess diethylenetriamine was distilled off under reduced pressure to give 25.06 g (97.2%) of 5-(dimethylaminomethyl-N- 2-[N'-(2-aminoethyl)amino]ethyl]-2-furancarboxamide (Compound l) as tan-brown oil.

NMR (CDCl$_3$) δ (ppm): 7.01 & 6.28 (each 1H, each d, J=3.1 Hz), 6.95 (1H, bs), 3.64 (2H, s), 3.50 (2H, m), 2.78 (6H, m), 2.40 (4H, m), 1.62 (6H, m), 1.48 (3H, bs)

Compound l was reduced in the same manner as Example 1 to give 5-(dimethylaminomethyl)-N-[2-[N'-(2-aminoethyl)amino]ethyl]furfurylamine (Compound m) as light yellow oil.

NMR (CDCl$_3$) δ (ppm): 6.75 (2H, s), 3.75 (2H, s), 3.41 (2H, s), 2.72 (8H, m), 2.26 (6H, s), 1.76 (4H, bs)

A mixture consisting of 2.0 g (8.33 mmol) of Compound m and 1.41 g (8.33 mmol) of [bis(methylthio)-methylene] propanedinitrile was heated at 80° C. with constant aspiration for 1 hour. The resulting reaction mixture was purified by silica gel column chromatography (chloroform-methanol = 10:1→chloroform-methanol-triethylamine 100:10:1) to give 1.59 g (61.1%) of Compound 22 as brown oil.

m.p.: 159°-160° C. (monofumarate)

Elemental analysis: C$_{16}$H$_{22}$N$_6$O.C$_4$H$_4$O$_4$ Calcd. (%): C 55.80, H 6.09, N 19.52. Found (%): C 55.76, H 6.18, N 19.79.

MS (m/z): 316 (M+)

NMR (D$_2$O) δ (ppm): 6.77 & 6.73 (each 1H, each d, J=2.93 Hz), 6.51 (2H, s), 4.41 (2H, s), 4.38 (2H, s), 3.89 & 3.38 (each 2H, each t, J=6.78, 6.96 Hz), 3.82 & 3.63 (each 2H, each t, J=8.42, 9.53 Hz), 2.89 (6H, s)

IR (KBr; cm$^{-1}$): 3200, 2900–2960, 2200, 2160

EXAMPLE 23

Synthesis of Compound 22 (alternative process)

A mixture consisting of 5.1 g (30 mmol) of bis(methylthio)methylene]propanedinitrile and 3.12 g (30 mmol) of N-(2-aminoethyl)ethanolamine was reacted at room temperature under constant aspiration for 2 hours. Then, 50 ml of pyridine and 8.60 g (45 mmol) of p-toluenesulfonyl chloride were added and the mixture was stirred at room temperature for 14 hours. The reaction mixture was diluted with 10 ml of water and stirred for 30 minutes, after which the solvent was distilled off and 50 ml of ice-water was added to the residue. The resulting precipitate was collected by filtration and washed with 30 ml of ethanol to give 7.46 g (74.9%) of [1-[(2-tosyloxy)ethyl]imidazolidinylidene)propanedinitrile (Compound n) as white crystals.

m.p.: 174°-176° C.

NMR (DMSO-d$_6$) δ (ppm): 7.93 (1H, bs), 7.88 & 7.45 (each 2H, each d, J=9.2 Hz), 4.23 (2H, t), 3.20-3.90 (6H, m), 2.44 (3H, s)

In 100 ml of dimethylformamide was dissolved 7.0 g (21.1 mmol) of Compound n and after addition of 6.9 g (105.4 mmol) of sodium azide, the mixture was heated at 60° C. for 2 hours. After cooling, the solvent was distilled off under reduced pressure and 100 ml of ethyl acetate was added to the residue. The insolubles were filtered off and the filtrate was washed with 70 ml of saturated aqueous sodium chloride solution twice. The organic layer was dried over anhydrous magnesium sulfate and the solvent was distilled off under reduced pressure. The resulting crude crystals were recrystallized from isopropyl alcohol to give 4.0 g (93.5%) of [1-[(2-azido)ethyl]imidazolidinylidene]propanedinitrile (Compound o) as light brown crystals.

m.p.: 108°-109° C.

NMR (CDCl$_3$) δ (ppm): 6.28 (1H, bs), 3.30-4.10 (8H, m)

In 120 ml of ethanol was dissolved 3.5 g (17.2 mmol) of Compound o with heating and a suspension of 180 mg (5 w/w%) of 10% palladium-carbon in 5 ml of water was added. The mixture was stirred under bubbling with hydrogen gas at room temperature for 4 hours. The catalyst was then filtered off and 1.2 g (10.3 mmol) of fumaric acid was added to the filtrate. The mixture was heated under reflux for 30 minutes. The precipitate separating out was collected by filtration and washed with ethanol to give 2.43 g (60.3%) of [1-(2-aminoethyl)imidazolidinylidene]propanedinitrile hemifumarate (Compound p) as light yellow crystals.

m.p.: 201°-203° C. (decompn.)

NMR (D$_2$O) δ (ppm): 6.40 (1H, s), 3.20-3.95 (6H, m), 2.93 (2H, t)

In 300 ml of ethanol was suspended 6.14 g (26.1 mmol) of Compound p followed by addition of a solution of 4.0 g (26.1 mmol) of 5-dimethylaminomethylfurfural in 50 ml of ethanol. Further 5.3 g (52.3 mmol) of triethylamine was added thereto and the mixture was stirred at room temperature for 15 hours. The reaction mixture was then ice-cooled and 1.2 g (31.4 mmol) of sodium borohydride was gradually added. The mixture was stirred under ice-cooling for 30 minutes, at the end of which time the solvent was distilled off. To the residue was added 300 ml of methylene chloride and the mixture was washed with 150 ml of saturated aqueous sodium chloride solution for a total of 4 times. The organic layer was dried over anhydrous magnesium sulfate and the solvent was then distilled off. Finally the residue was purified by silica gel column chromatography (ethyl acetate-methanol-triethylamine 200:20:1→2:1) to give 5.49 g (66.9%) of Compound 22 as light brown oil.

In the following Example 24 through 43, the respective compounds were produced in accordance with the procedure set forth in Example 12, 22 or 23.

EXAMPLE 24

Diethyl [1-[2-[(5-dimethylaminomethyl-2-furanyl)-methylamino]ethyl]-2-imidazolidinylidene]malonate (Compound 23)

Elemental analysis: C$_{20}$H$_{32}$N$_4$O$_5$.H$_2$O Calcd. (%): C 56.32, H 8.04, N 14.32. Found (%): C 56.47, H 8.35, N 14.63.

MS (m/z): 409 (M+1)

NMR (CDCl$_3$) δ (ppm): 8.36 (1H, bs), 6.05 (2H, s), 4.12 (4H, q) 3.70 (4H, m), 3.59 (2H, t), 3.56 (2H, s), 3.37 (2H, s), 2.81 (2H, t), 2.23 (6H, s), 1.26 (6H, t)

IR (KBr; cm-1): 3400, 2950, 1740, 1200

EXAMPLE 25

[1-[2-[(5-Dimethylaminomethyl-2-furanyl)-methylamino]ethyl]-2-imidazolidinylidene]nitromethane (Compound 24)

m.p. 150°-151° C. (decomp.) (difumarate)

Elemental analysis: C$_4$H$_{23}$N$_5$O$_3$.2C$_4$H$_4$O$_4$.1/5H$_2$O Calcd. (%): C 48.47, H 5.81, N 12.85. Found (%): C 48.65, H 5.80, N 12.48.

MS (m/z): 292 (M+-OH)

NMR (CDCl$_3$) δ (ppm): 8.60 (1H, bs), 6.52 (1H, s), 6.08 (2H, s), 3.74 (2H, s), 3.71 (4H, s), 3.42 (2H, s), 3.22 (2H, t), 2.79 (2H, t), 2.25 (6H, s), 2.18 (1H, bs)

IR (KBr; cm$^{-1}$): 3400, 2950, 1580

EXAMPLE 26

[1-[2-[(5-Ethylmethylaminomethyl-2-furanyl)methylamino]ethyl]-2-imidazolidinylidene]propanedinitrile (Compound 25)

m.p.: 107°–111° C. (monofumarate)

Elemental analysis: $C_{17}H_{24}N_6O \cdot C_4H_4O_4 \cdot 2/5H_2O$ Calcd. (%): C 55.84, H 6.43, N 18.61. Found (%): C 55.62, H 6.31, N 18.32.

MS (m/z): 328 (M$^+$)

NMR (CDCl$_3$) δ (ppm): 6.13 (1H, bs), 6.08 (2H, s), 3.77 (2H, s), 3.65 (6H, m), 3.49 (2H, s), 2.90 (2H, t), 2.45 (2H, q), 2.23 (3H, s), 1.77 (1H, bs), 1.08 (3H, t)

IR (KBr; cm$^{-1}$): 3400, 2930, 2200, 2160

EXAMPLE 27

[1-[2-[(5-Diethylaminomethyl-2-furanyl)methylamino]ethyl]-2-imidazolidinylidene]propanedinitrile (Compound 26)

m.p.: 115°–118° C. (dihydrochloride)

Elemental analysis: $C_{18}H_{26}N_6O \cdot 2HCl \cdot H_2O$ Calcd. (%): C 49.89, H 6.98, N 19.39. Found (%): C 49.60, H 7.22, N 19.101.

MS (m/z): 342 (M$^+$)

NMR (CDCl$_3$) δ (ppm): 6.07 (2H, s), 5.83 (1H, bs), 3.76 (2H, s), 3.59 (2H, s), 3.50–3.96 (6H, m), 2.91 (2H, t), 2.54 (4H, q), 1.72 (1H, bs), 1.06 (6H, t)

IR (KBr; cm$^{-1}$): 3350, 2930, 2200, 2160

EXAMPLE 28

[1-[2-[(5-Pyrrolidinylmethyl-2-furanyl)methylamino]ethyl]-2-imidazolidinylidene]propanedinitrile (Compound 27)

m.p. 122°–126° C. (decomp.) (monofumarate)

Elemental analysis: $C_{18}H_{24}N_6O \cdot C_4H_4O_4 \cdot H_2O$ Calcd. (%): C 55.69, H 6.37, N 17.71. Found (%): C 55.60, H 6.36, N 17.99.

MS (m/z): 340 (M$^+$)

NMR (CDCl$_3$) δ (ppm): 6.07 (2H, s), 5.85 (1H, bs), 3.76 (2H, s), 3.57 (2H, s), 3.40–3.95 (6H, m), 2.88 (2H, t), 2.53 (4H, m), 1.77 (4H, m)

IR (KBr; cm$^{-1}$): 3400, 2950, 2200, 2160

EXAMPLE 29

[1-[2-[(5-Piperidinomethyl-2-furanyl)methylamino]ethyl]-2-imidazolidinylidene]propanedinitrile (Compound 28)

m.p.: 149°–151° C. (monofumarate)

Elemental analysis: $C_{19}H_{26}N_6O \cdot C_4H_4O_4$ Calcd (%) C 58.71, H 6.43, N 17.86. Found (%): C 58.79, H 6.57, N 17.88.

MS (m/z): 354 (M$^+$)

NMR (CDCl$_3$) δ (ppm): 6.06 (2H, s), 5.79 (1H, bs), 3.75 (2H, s), 3.57 (2H, s), 3.40–3.90 (6H, m), 2.89 (2H, t), 2.44 (4H, m), 1.60 (6H, m)

IR (KBr; cm$^{-1}$): 3350, 2950, 2200, 2160

EXAMPLE 30

[1-[2-[(5-Perhydroazepinylmethyl-2-furanyl)methylamino]ethyl]-2-imidazolidinylidene]propanedinitrile (Compound 29)

Elemental analysis: $C_{20}H_{28}N_6O \cdot 2HCl \cdot C_2H_6O$ Calcd. (%): C 54.21, H 7.44, N 17.24. Found (%): C 54.16, H 7.56, N 17.45.

MS (m/z): 368 (M$^+$)

NMR (CDCl$_3$) δ (ppm): 6.08 (2H, s), 5.64 (1H bs), 3.76 (2H, s), 3.64 (2H, s), 3.40–4.00 (6H, m), 2.90 (2H, t), 2.68 (4H, m), 1.75 (8H, m)

IR (KBr; cm$^{-1}$): 3400, 2940, 2200, 2160

EXAMPLE 31

[1-[2-[[5-(2-Methylpiperidinomethyl)-2-furanyl]methylamino]ethyl]-2-imidazolidinylidene]propanedinitrile (Compound 30)

m.p.: 132°–135° C. (decomp.) (3/2 fumarate)

Elemental analysis: $C_{20}H_{28}N_6O \cdot 3/2C_4H_4O_4 \cdot \frac{1}{2}H_2O$ Calcd. (%): C 56.61, H 6.40, N 15.24. Found (%): C 56.40, H 6.29, N 15.55.

MS (m/z): 368 (M$^+$)

NMR (CDCl$_3$) δ (ppm): 6.10 & 6.05 (each 1H, each d, J=3.31 Hz), 3.76 (2H, s), 3.66 (2H, s), 3.40–4.00 (6H, m), 2.89 (2H, t), 2.80 (1H, m), 1.17 (3H, d), 1.0–2.4 (8H, m)

IR (KBr; cm$^{-1}$): 3400, 2930, 2200, 2160

EXAMPLE 32

[1-[2-[[5-(3-Methylpiperidinomethyl)-2-furanyl]methylamino]ethyl]-2-imidazolidinylidene]propanedinitrile (Compound 31)

m.p.: 126°–129° C. (3/2 fumarate)

Elemental analysis: $C_{20}H_{28}N_6O \cdot 3/2C_4H_4O_4 \cdot 2/5H_2O$ Calcd. (%): C 56.80, H 6.38, N 15.29. Found (%): C 56.84, H 6.41, N 15.03.

MS (m/z): 368 (M$^+$)

NMR (CDCl$_3$) δ (ppm): 6.09 (2H, s), 5.77 (1H, bs), 3.77 (2H, s), 3.46 (2H, s), 3.40–4.00 (6H, m), 2.91 (2H, t), 2.80 (2H, m), 1.35–2.05 (8H, m), 1.41 (3H, d)

IR (KBr; cm$^{-1}$): 3400, 2930, 2200, 2160

EXAMPLE 33

[1-[2-[[5-(4-Methylpiperidinomethyl)-2-furanyl]methylamino]ethyl]-2-imidazolidinylidene]propanedinitrile (Compound 32)

m.p.: 145°–147° C. (monofumarate)

Elemental analysis: $C_{20}H_{28}N_6O \cdot C_4H_4O_4 \cdot 1/5C_8H_8O$ Calcd. (%): C 59.50, H 6.82, N 16.92. Found (%): C 59.20, H 6.73, N 16.78.

MS (m/z): 368 (M$^+$)

NMR (CDCl$_3$) δ (ppm): 6.07 (2H, s), 5.65 (1H, bs), 3.86 (2H, s), 3.46 (2H, s), 3.40–4.00 (6H, m), 2.89 (2H, t), 2.84 (2H, m), 1.10–2.20 (8H, m), 1.89 (3H, bd)

IR (KBr; cm$^{-1}$): 3400, 2930, 2200, 2160

EXAMPLE 34

[1-[2-[[5-(2,6-Dimethylpiperidinomethyl)-2-furanyl]methylamino]ethyl]-2-imidazolidinylidene]propanedinitrile (Compound 33)

m.p.: 96°–97° C.

Elemental analysis: $C_{21}H_{30}N_6O \cdot 3/5H_2O$ Calcd. (%): C 64.13, H 8.00, N 21.37. Found (%): C 64.01, H 8.02, N 21.60.

MS (m/z): 382 (M$^+$)

NMR (CDCl$_3$) δ (ppm): 6.12 & 6.07 (each 1H, each d, J=3.2 Hz), 5.81 (1H, bs), 3.97 (2H, s), 3.78 (2H, s), 3.45–4.15 (6H, m), 2.94 (2H, t), 2.36 (2H, m), 1.10–1.80 (7H, m), 1.26 (6H, d)

IR (KBr; cm$^{-1}$): 3400, 2950, 2200, 2160

EXAMPLE 35

[1-[2-[[5-(3-Methoxypiperidinomethyl)-2-furanyl]methylamino]ethyl]-2-imidazolidinylidene]propanedinitrile (Compound 34)

Elemental analysis: $C_{20}H_{28}N_6O_2.2HCl.4/5C_2H_6O$
Calcd. (%): C 52.49, H 7.10, N 17.00. Found (%): C 52.62, H 7.32, N 16.72.
MS (m/z): 384 (M+)
NMR (CDCl₃) δ (ppm): 6.09 (2H, s), 5.92 (1H, bs), 3.76 (2H, s), 3.53 (2H, s), 3.46–4.10 (6H, m), 3.33 (3H, s), 3.30 (1H, m), 2.90 (2H, t), 2.50–2.90 (2H, m), 1.10–2.30 (7H, m)
IR (KBr; cm⁻¹): 3250, 2940, 2200, 2160, 1200, 1100

EXAMPLE 36

[1-[2-[[5-(4-methoxypiperidinomethyl)-2-furanyl]methylamino]ethyl]-2-imidazolidinylidene]propanedinitrile (Compound 35)

Elemental analysis: $C_{20}H_{28}N_6O_2.2HCl.H_2O$ Calcd. (%): C 50.53, H 6.78, N 17.68. Found (%): C 50.81, H 6.90, N 17.43.
MS (m/z): 384 (M+)
NMR (CDCl₃) δ (ppm): 6.08 (2H, s), 5.76 (1H, bs), 3.76 (2H, s), 3.47 (2H, s), 3.40–4.10 (6H, m), 3.19 (1H, m), 2.89 (1H, t), 2.69 (2H, m), 1.35–2.40 (7H, m)
IR (KBr; cm⁻¹): 3400, 2980, 2200, 2160, 1210, 1100

EXAMPLE 37

[1-[2-[[5-[1-(1,2,3,6-Tetrahydro)pyridylmethyl]-2-furanyl]methylamino]ethyl]-2-imidazolidinylidene]propanedinitrile (Compound 36)

Elemental analysis: $C_{19}H_{24}N_6O.2HCl.H_2O.4/5C_2H_6O$ Calcd. (%): C 51.52, H 6.88, N 17.50. Found (%): C 51.41, H 7.06, N 17.56.
MS (m/Z): 352 (M+)
NMR (CDCl₃) δ (ppm): 6.11 (2H, s), 6.02 (1H, bs), 5.66 (2H, m), 3.77 (2H, s), 3.58 (2H, s), 340–4.10 (6H, m), 2.96 (2H, m), 2.89 (2H, t), 2.60 (2H, m), 2.19 (2H, m), 1.70 (1H, bs)
IR (KBr; cm⁻¹): 3400, 2950, 2200, 2160, 1630

EXAMPLE 38

[1-[2-[(5-Morpholinomethyl-2-furanyl)methylamino]ethyl]-2-imidazolidinylidene]propanedinitrile (Compound 37)

m.p.: 154.5°–155.5° C. (hemifumarate)
Elemental analysis: $C_{18}H_{24}N_6O_2.\frac{1}{2}C_4H_4O_4.1/5H_2O$ Calcd. (%): C 57.46, H 6.36, N 20.10. Found (%): C 57.74, H 6.46, N 19.82.
MS (m/z): 356 (M+)
NMR (CDCl₃) δ (ppm): 6.12 (2H, s), 6.06 (1H, bs), 3.88 (2H, s), 3.50 (2H, s), 3.40–4.05 (10H, m), 2.90 (2H, t), 2.47 (4h, m), 1.76 (1H, bs)
IR (KBr; cm⁻¹): 3230, 2900–2950, 2200, 2170, 1200, 1100

EXAMPLE 39

[1-[2-[[(5-Thiomorpholinomethyl-2-furanyl)methylamino]ethyl]-2-imidazolidinylidene]propanedinitrile (Compound 38)

m.p.: 152°–153° C. (monofumarate)
Elemental analysis: $C_{18}H_{24}N_6OS.C_4H_4O_4.1/5H_2O$ Calcd. (%): C 53.69, H 5.82, N 17.08. Found (%): C 53.53, H 5.80, N 16.89.
MS (m/z): 372 (M+)
NMR (CDCl₃) δ (ppm): 6.11 (2H, s), 6.01 (1H, bs), 3.79 (2H, s), 3.48 (2H, s), 3.40–4.10 (6H, m), 2.91 (2H, t), 2.69 (8H, m), 1.81 (1H, bs)
IR (KBr; cm⁻¹): 3400, 2920, 2200, 2160

EXAMPLE 40

[1-[2-[[5-[N-(N'-Methyl)piperadinylmethyl]-2-furanyl]methylamino]ethyl]-2-imidazolidinylidene]propanedinitrile (Compound 39)

m.p.: 126°–128° C. (5/2 fumarate)
Elemental analysis: $C_{19}H_{27}N_7O.5/2C_4H_4O_4$ Calcd. (%): C 52.80, H 5.65, N 14.86. Found (%): C 52.65, H 5.76, N 14.82.
MS (m/z): 369 (M+)
NMR (CDCl₃) δ (ppm): 6.12 (1H, bs), 6.10 (2H, s), 3.76 (2H, s), 3.52 (2H, s), 3.40–4.00 (6H, m), 2.89 (2H, t), 2.49 (8H, bs), 2.27 (3H, s), 2.04 (1H, bs)
IR (KBr; cm⁻¹); 3220, 2900–2950, 2200, 2160

EXAMPLE 41

[1-[2-[(2-Furanyl)methylamino]ethyl]-2-imidazolidinylidene]propanedinitrile (Compound 40)

m.p.: 125.5°–126° C.
Elemental analysis: $C_{13}H_{15}N_5O$ Calcd. (%): C 60.68, H 5.88, N 27.22. Found (%): C 60.91, H 5.84, N 26.98.
MS (m/z): 257 (M+)
NMR (DMSO-d₆) δ (ppm): 7.85 (1H, bs), 7.54 (1H, dd, J=1.83, 0.92 Hz), 6.37 (1H, dd, J=1.83, 3.11 Hz), 6.24 (1H, dd, J=0.92, 3.11 Hz), 3.73 (2H, t, J=8.61, 9.71 Hz), 3.70 (2H, s), 3.53 (2H, t J=6.41, 623 Hz), 3.43 (2H, t, J=8.61, 9.71 Hz), 2.74 (2H, t, J=6.42, 6.22 Hz), 2.26 (1H, bs)
IR (KBr; cm⁻¹): 3330, 2950 2200, 2160

EXAMPLE 42

[1-[2-[[5-(3-Hydroxypiperidinomethyl)-2-furanyl]methylamino]ethyl]-2-imidazolidinylidene]propanedinitrile (Compound 41)

Elemental analysis: $C_{19}H_{26}N_6O_2.C_4H_4O_4.\frac{1}{2}H_2O$ Calcd. (%): C 55.75, H 6.31, N 16.96. Found (%): C 55.81, H 6.28, N 17.09.
MS (m/z): 370 (M+), 352 (M+—H₂O)
NMR (CDCl₃) δ (ppm): 6.16 (1H, bs), 6.09 (2H, s), 3.76 (2H, s), 3.54 (2H, s), 3.40–4.00 (7H, m), 3.89 (2H, t), 2.10–2.70 (4H, m), 1.25–1.95 (4H, m)
IR (KBr; cm⁻¹): 3330, 2980, 2200, 2160, 1070

EXAMPLE 43

[1-[2-[[5-(4-Hydroxypiperidinomethyl)-2-furanyl]methylamino]ethyl]-2-imidazolidinylidene]propanedinitrile (Compound 42)

m.p.: 122.5°–123.5° C.
Elemental analysis: $C_{19}H_{26}N_6O_2$ Calcd. (%) C 61.60, H 7.07, N 22.69. Found (%): C 61.42, H 7.29, N 23.00.
MS (m/z): 370 (M+), 352 (M+-H₂O)
NMR (CDCl₃) δ (ppm) 6.54 (1H, bs), 6.10 (2H, s), 3.76 (2H, s), 3.50 (2H, s), 3.30–3.95 (7H, m), 2.88 (2H, t), 2.77 (2H, m), 2.32 (2H, bs), 2.19 (2H, m), 1.80 (4H, m)
IR (KBr; cm⁻¹): 3340, 2980, 2200, 2160, 1020

EXAMPLE 44

[1-[2-[(5-Piperidinomethyl-2-furanyl)methylamino]ethyl]-3-methyl-2-imidazolidinylidene]propanedinitrile (Compound 43)

In 20 ml of dimethylformamide was dissolved 2.0 g (9.85 mmol) of [1-[(2-azido)ethyl]imidazolidinylidene]propanedinitrile, and under ice-cooling, 520 mg (13.0 mmol) of 60% sodium hydride was gradually added. After foaming had subsided, 2.8 g (19.7 mmol) of methyl iodide was added dropwise with constant stirring and ice-cooling. The reaction mixture was further stirred at room temperature for 30 minutes, after which it was diluted with 3 ml of water and concentrated under reduced pressure. To the residue was added 30 ml of ethyl acetate and the mixture was washed with 3 portions of saturated aqueous sodium chloride solution and dried over anhydrous magnesium sulfate. The solvent was then distilled off under reduced pressure and the residue was purified by silica gel column chromatography (chloroform-methanol =100:1) to give 1.99 g (93.2%) of [1-[(2azido)ethyl]-3-methyl-2-imidazolidinylidene]propanedinitrile (Compound g) as light yellow oil.

NMR (CDCl$_3$) δ (ppm): 3.69 (8H, m), 3.20 (3H, s)

In 50 ml of toluene were dissolved 1.7 g (7.8 mmol) of Compound g and 2.46 g (9.4 mmol) of triphenylphosphine, and after addition of 1.4 ml of water, the mixture was stirred at 50° C. for 1.5 hours. The reaction mixture was then concentrated and the residue was dissolved in 40 ml of ethanol. Then, 550 mg (4.7 mmol) of fumaric acid was added and the mixture was heated under reflux for 30 minutes. The reaction mixture was then stirred with ice-cooling for 30 minutes and the resulting crystals were collected by filtration to give 1.39 g (71.3%) of [1-(2-aminoethyl)-3-methyl-2-imidazolidinylidene]-propanedinitrile hemifumarate (Compound r) as white crystals.

m.p.: 163.5°–165° C.

NMR (D$_2$O) δ (ppm): 6.44 (1H, s), 3.3–3.9 (6H, m), 3.07 (3H, s), 2.97 (2H, t)

Using Compound r and 5-piperidinomethylfurfural, the corresponding procedure of Example 23 was followed to give Compound 43 as light tan-colored oil.

Elemental analysis: C$_{20}$H$_{28}$N$_6$O.2HCl.H$_2$O Calcd. (%): C 52.29, H 7.02, N 18.29. Found (%): C 52.40, H 7.00, N 18.01.

MS (m/z): 368 (M+)

NMR (CDCl$_3$) δ (ppm): 6.06 (2H, s), 3.63 (6H, m), 3.45 (2H, s), 3.16 (3H, s), 2.89 (2H, t), 2.38 (4H, m), 1.81 (1H, bs), 1.50 (6H, m)

IR (KBr; cm$^{-1}$): 3340, 2950, 2200, 2160

EXAMPLE 45

[1-[2-[N-(Acetyl)-N-[(5-piperidinomethyl-2-furanyl)-methyl]amino]ethyl]-2-imidazolidinylidene]-propanedinitrile (Compound 44)

In 12 ml of pyridine was dissolved 0.6 g (1.69 mmol) of Compound 28, and 260 mg (2.55 mmol) of acetic anhydride was added dropwise. The reaction mixture was stirred at room temperature for 0.5 hour and, after addition of 1 ml of methanol, the solvent was distilled off. The residue was diluted with 20 ml of water, adjusted to pH 13 with 5N sodium hydroxide solution and extracted with methylene chloride. The extract was washed with saturated aqueous sodium chloride solution twice and dried over anhydrous magnesium sulfate. Finally the solvent was distilled off to give 0.66 g (97.9%) of Compound 44 as colorless oil.

m.p.: 166°–167° C. (monofumarate)

Elemental analysis: C$_{21}$H$_{28}$N$_6$O$_2$.C$_4$H$_4$O$_4$ Calcd. (%): C 58.58, H 6.29, N 16.40. Found (%): C 58.78, H 6.34, N 16.53.

MS (m/z): 396 (M+), 353 (M+—COCH3)

NMR (CDCl$_3$) δ (ppm): 6.22 & 6.09 (each 1H, each d, J=3.2 Hz), 5.83 (1H, bs), 4.51 (2H, s), 3.5–4.0 (8H, m), 3.46 (2H, s), 2.40 (4H, m), 2.23 (3H, s), 1.48 (6H, m)

IR (KBr; cm$^{-1}$): 3320, 2950, 2200, 2160, 1690

EXAMPLE 46

[1-[2-[N-(Methyl)-N-[(5-piperidinomethyl-2-furanyl)-methyl]amino]ethyl]-2-imidazolidinylidene]-propanedinitrile (Compound 45)

In 15 ml of acetonitrile were dissolved 904 mg (2.55 mmol) of Compound 28 and 1 ml (12.3 mmol) of 37% aqueous formalin followed by gradual addition of 271 mg (4.30 mmol) of sodium cyanoborohydride at room temperature. The reaction mixture was stirred at room temperature for 30 minutes and, then, adjusted to pH 7.2 with acetic acid. The reaction mixture was further stirred at room temperature for 45 minutes, at the end of which time the solvent was distilled off under reduced pressure. The residue was diluted with 2N sodium hydroxide solution and extracted with methylene chloride. The organic layer was washed with 0.1N sodium hydroxide solution once and, then, extracted with 1N hydrochloric acid twice. The aqueous layer was adjusted to pH 7.8 with 1N sodium hydroxide solution and re-extracted with 4 portions of methylene chloride. The pooled organic layer was dried over anhydrous magnesium sulfate and the solvent was distilled off. Finally the residue was purified by silica gel column chromatography (chloroform-methanol=10:1) to give 244 mg (26.0%) of Compound 45 as colorless oil.

m.p.: 140°–143° C. (difumarate)

Elemental analysis: C$_{20}$H$_{28}$N$_6$O.2C$_4$H$_4$O$_4$.3/5H$_2$O Calcd. (%): C 55.00, H 6.13, N 13.74. Found (%): C 55.06, H 5.90, N 13.46.

MS (m/z): 368 (M+)

NMR (D$_2$O) δ (ppm): 6.85 & 6.79 (each 1H, each d, J=3.29 Hz), 6.68 (4H, s), 4.52 (2H, s), 4.37 (2H, s), 3.94 (2H, t, J=7.5 Hz), 3.80 (2H, m), 3.63 (2H, m), 3.48 (4H, m), 2.99 (2H, t, J=7.5 Hz), 2.94 (3H, s) 1.35–2.05 (6H, m)

IR (KBr; cm$^{-1}$): 3320, 2950, 2200, 2160

EXAMPLE 47

[1-[1-[(5-Piperidinomethyl-2-furanyl)methyl]-piperidinyl-4-amino](methylamino)methylene]-propanedinitrile (Compound 46)

In 45 ml of dimethylformamide was dissolved 6.0 g (31.8 mmol) of ethyl 5-chloromethyl-2-furancarboxylate followed by addition of 9.64 g (95.5 mmol) of 4-hydroxypiperidine and the mixture was stirred at room temperature for 20 hours. The solvent was then distilled off under reduced pressure and the residue was diluted with 100 ml of chloroform and washed with saturated aqueous sodium chloride solution twice. The organic layer was dried over anhydrous magnesium sulfate and the solvent was distilled off to give 7.84 g (97.4%) of ethyl 5-(4-hydroxypiperidinomethyl)-2-furancarboxylate (Compound s) as light brown oil.

NMR (CDCl$_3$) δ (ppm): 7.08 & 6.27 (each 1H, each d, J=3.1 Hz), 4.32 (2H, q), 3.65 (1H, m), 3.59 (2H, s), 2.80 (2H, m), 2.24 (2H, m), 1.4–2.06 (4H, m), 1.36 (3H, t)

In 30 ml of piperidine was dissolved 7.4 g (29.25 mmol) of Compound s followed by addition of 2.7 g (45 mmol) of acetic acid, and the mixture was heated under reflux for 27 hours. After cooling, the excess piperidine was distilled off under reduced pressure and the residue was diluted with 300 ml of chloroform and washed with 3 portions of saturated aqueous sodium chloride solution. The organic layer was dried over anhydrous magnesium sulfate and the solvent was distilled off under reduced pressure. Finally the residue was purified by silica gel column chromatography (acetone) to give 6.49 g (76.0%) of 1-[5-(4-hydroxypiperidinomethyl)-2-furancarbonyl]piperidine (Compound t) as light yellow oil.

NMR (CDCl$_3$) δ (ppm): 6.82 & 6.23 (each 1H, each d, J=3.2 Hz), 3.65 (5H, m), 3.58 (2H, s), 2.76 (2H, m), 2.22 (2H, m), 1.2–2.0 (10H, m)

In 70 ml of pyridine was dissolved 3.47 g (11.88 mmol) of Compound t and with ice-cooling, 1.9 ml (23.77 mmol) of methanesulfonyl chloride was added dropwise. The mixture was stirred at 0° C. for 4.5 hours and, after addition of 5 ml of methanol, stirred at room temperature for 30 minutes. The solvent was then distilled off under reduced pressure and the residue was dissolved in 100 ml of methylene chloride. This solution was washed with 3 portions of saturated aqueous sodium chloride solution. The organic layer was dried over anhydrous magnesium sulfate and the solvent was distilled off under reduced pressure to give 4.04 g (91.8%) of 1-[5-(4-mesyloxypiperidinomethyl)-2-furancarbonyl]piperidine (Compound u) as red-brown oil.

NMR (CDCl$_3$) δ (ppm): 6.80 & 6.23 (each 1H, each d, J=3.1 Hz), 4.70 (1H, m), 3.65 (4H, m), 3.57 (2H, s), 2.99 (3H, s), 2.71 (2H, m), 2.38 (2H, m), 1.98 (4H, m), 1.66 (6H, m)

In 90 ml of dimethylformamide were dissolved 4.04 g (10.9 mmol) of Compound u and 7.1 g (109.2 mmol) of sodium azide and the solution was heated at 120° C. for 1.5 hours. The reaction mixture was allowed to stand for cooling and, then, the insolubles were filtered off. The filtrate was concentrated under reduced pressure. The residue was diluted with 120 ml of ethyl acetate and washed with 3 portions of saturated aqueous sodium chloride solution. The organic layer was dried over anhydrous magnesium sulfate. The solvent was then distilled off and the residue was purified by silica gel column chromatography (chloroform-methanol=30:1) to give 2.28 g (65.9%) of 1-[5-(4-azidopiperidinomethyl)-2-furancarbonyl]piperidine (Compound v) as light yellow oil.

NMR (CDCl$_3$) δ (ppm): 6.81 & 6.23 (each 1H, each d, J=3.1 Hz), 3.67 (4H, m), 3.58 (2H, s), 3.37 (1H, m), 2.79 (2H, m), 2.27 (2H, m), 1.84 (4H, m), 1.67 (6H, m)

In 100 ml of dry tetrahydrofuran was suspended 1.1 g (28.8 mmol) of lithium aluminum hydride, and under nitrogen stream a solution of 2.28 g (7.2 mmol) of Compound v in 50 ml of dry tetrahydrofuran was added dropwise at room temperature. After completion of dropwise addition, the mixture was heated under reflux for 20 hours. The reaction mixture was ice-cooled and 2.2 ml of water, 1.1 ml of 20% aqueous sodium hydroxide solution and 5.5 ml of water were serially added gradually. The mixture was stirred at 0° C. for 30 minutes. The insolubles were then filtered off, the filtrate was concentrated under reduced pressure, and the residue was subjected to vacuum distillation (160°–180° C./1 mmHg) to give 1.82 g (91.5%) of 2-(4-aminopiperidinomethyl)-5-piperidinomethylfuran (Compound w) as light yellow oil.

NMR (CDCl$_3$) δ (ppm): 6.07 (2H, s), 3.50 (2H, s), 3.47 (2H, s), 2.79 (2H, m), 2.61 (1H, m), 2.38 (4H, m), 2.04 (2H, m), 1.1–1.9 (12H, m)

A mixture consisting of 1.8 g (6.5 mmol) of Compound w and 930 mg (6.5 mmol) of [(methylthio)-(methylamino)methylene]malononitrile was heated under constant aspiration at 80° C. for 1.5 hours. The reaction mixture was then purified by silica gel column chromatography (chloroform-methanol=10:1) to give 1.04 g (41.9%) of Compound 46 as light yellow foam.

Elemental analysis: C$_{21}$H$_{30}$N$_6$O.2HCl.C$_2$H$_6$O Calcd. (%): C 55.08, H 7.64, N 16.76. Found (%): C 55.23, H 7.77, N 16.9.

MS (m/z): 382 (M+)

NMR (CDCl$_3$) δ (ppm): 6.08 (2H, s), 5.73 (1H, bq), 4.97 (1H, bd), 3.69 (1H, m), 3.48 (2H, s), 3.46 (2H, s), 2.97 (3H, d), 2.83 (2H, bd), 2.40 (4H, m), 2.06 (4H, m), 1.2–1.85 (8H, m)

IR (KBr; cm$^{-1}$): 3400, 2850, 2200, 2160

EXAMPLE 48

[[1-[(5-Piperidinomethyl-2-furanyl)methyl]-piperidinyl-3-amino](methylamino)methylene]propanedinitrile (Compound 47)

Using ethyl 5-chloromethyl-2-furancarboxylate and 3-hydroxypiperidine, the procedure of Example 47 was followed to give Compound 47 in 6 steps.

m.p.: 138.5°–140° C.

Elemental analysis: C$_{21}$H$_{30}$N$_6$O Calcd. (%): C 65.95, N 7.91, N 21.97. Found (%): C 65.95, H 8.10, N 21.87.

MS (m/z): 382 (M+)

NMR (CDCl$_3$) δ (ppm): 9.60 (1H, bs), 6.15 (2H, s), 5.74 (1H, bt), 3.77 & 3.56 (each 1H, each d, J=13.83 Hz), 3.44 (2H, s), 3.12 (3H, d), 3.0–3.2 (2H, m), 2.97 (1H, m), 2.86 (1H, m), 2.46 (1H, m), 2.39 (4H, m), 1.6–2.0 (4H, m), 1.58 (4H, m), 1.43 (2H, m)

IR (KBr; cm$^{-1}$): 3320, 2930, 2200, 2160

In the following Examples 49 and 50, the respective compounds were produced generally in accordance with the procedure described in Example 12.

EXAMPLE 49

[1-[2-[(2-Piperidinomethyl-3-furanyl)methylamino]ethyl]-2-imidazolidinylidene]propanedinitrile (Compound 48)

m.p.: 145.5°–147° C. (monofumarate)

Elemental analysis: C$_{19}$H$_{26}$N$_6$O.C$_4$H$_4$O$_4$ Calcd. (%): C 58.71, H 6.43, N 17.86. Found (%): C 58.66, H 6.31, N 17.69.

MS (m/z): 354 (M+)

NMR (CDCl$_3$) δ (ppm): 7.25 & 6.31 (each 1H, each d, J=1.98 Hz), 5.96 (1H, bs), 3.69 (6H, m), 3.64 (2H, s), 3.47 (2H, s), 2.91 (2H, t), 2.38 (4H, m), 1.58 (6H, m)

IR (KBr; cm$^{-1}$): 3450, 2850, 2190, 2170

EXAMPLE 50

[1-[2-[(3-Piperidinomethyl-2-furanyl)methylamino]ethyl]-2-imidazolidinylidene]propanedinitrile (Compound 49)

m.p.; 131°–132.5° C. (difumarate)

Elemental analysis: C$_{19}$H$_{26}$N$_6$O.2C$_4$H$_4$O$_4$.½C$_2$H$_6$O.½H$_2$O Calcd. (%): C 54.19, H 6.26, N 13.44. Found (%): C 54.22, H 6.47, N 13.55.

MS (m/z): 354 (M+)

NMR (CDCl$_3$) δ (ppm): 7.21 & 6.25 (each 1H, each d, J=1.88 Hz), 5.76 (1H, bs), 3.74 (2H, s), 3.62 (6H, m), 3.26 (2H, s), 2.85 (2H, t), 2.35 (4H, m), 1.92 (1H, bs), 1.46 (6H, m)

IR (KBr; cm$^{-1}$): 3400, 2830, 2190, 2160

In the following Examples 51 and 52, the respective compounds were produced generally in accordance with the procedure described in Example 22 or 23.

EXAMPLE 51

[1-[2-[(2-Piperidinomethyl-4-furanyl)methylamino]ethyl]-2-imidazolidinylidene]propanedinitrile (Compound 50)

m.p.: 148°–149° C. (monofumarate)

Elemental analysis: $C_{19}H_{26}N_6O \cdot C_4H_4O_4$ Calcd. (%): C 58.71, H 6.43, N 17.86. Found (%): C 54.48, H 6.78, N 17.89.

MS (m/z): 354 (M+)

NMR (CDCl$_3$) δ (ppm): 7.25 (1H, s), 6.14 (1H, s), 5.98 (1H, bs), 3.67 (6H, m), 3.63 (2H, s), 3.46 (2H, s), 2.92 (2H, t), 2.41 (4H, m), 1.53 (6H, m)

IR (KBr; cm$^{-1}$): 3400, 2900, 2190, 2150

EXAMPLE 52

[1-[2-[(4-Piperidinomethyl-2-furanyl)methylamino]ethyl]-2-imidazolidinylidene]propanedinitrile (Compound 51)

m.p.: 106°–109° C. (monofumarate)

Elemental analysis: $C_{19}H_{26}N_6O \cdot C_4H_4O_4 \cdot \frac{1}{2}C_2H_6O \cdot H_2O$ Calcd. (%): C 56.35, H 6.90, N 16.43. Found (%): C 56.31, H 6.99, N 16.10.

MS (m/z): 354 (M+)

NMR (CDCl$_3$) δ (ppm): 7.19 (1H, s), 6.28 (1H, bs), 6.16 (1H, s), 3.74 (2H, s), 3.63 (6H, m), 3.29 (2H, s), 2.90 (2H, t), 2.37 (4H, m), 1,49 (6H, m)

IR (KBr; cm$^{-1}$): 3400, 2850, 2190, 2160

REFERENCE EXAMPLE 1

Tablet

Tablets of the following composition are prepared by the established pharmaceutical procedure.

| | |
|---|---|
| Compound 2 | 150 mg |
| Lactose | 60 mg |
| Potato starch | 30 mg |
| Polyvinyl alcohol | 2 mg |
| Magnesium stearate | 1 mg |
| Tar color | trace |

REFERENCE EXAMPLE 2

Powder

A powder of the following composition is prepared by the established pharmaceutical procedure.

| | |
|---|---|
| Compound 24 | 200 mg |
| Lactose | 270 mg |

REFERENCE EXAMPLE 3

Syrup

A syrup of the following composition is prepared by the established pharamceutical procedure.

| | |
|---|---|
| Compound 28 | 200 mg |
| Purified sucrose | 40 g |
| Ethyl p-hydroxybenzoate | 40 mg |
| Propyl p-hydroxybenzoate | 10 mg |
| Strawberry flavor | 0.1 cc |
| Water to make | 100 cc |

While the invention has been described in detail and with reference to specific embodiments thereof, it will be apparent to one skilled in the art that various changes and modifications can be made therein without departing from the spirit and scope thereof.

What is claimed is:

1. A furan derivative of the formula

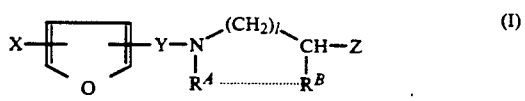

wherein X is $R^1CH_2$— where $R^1$ is $R^2R^3N$—, where $R^2$ and $R^3$ are the same or different and each is hydrogen or lower alkyl, or $R^2$ and $R^3$, taken together with the adjacent nitrogen atom, represent a heterocyclic group of the formula

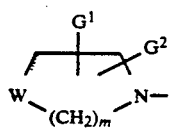

wherein ═ means a single bond or a double bond, and when ═ is a single bond, W represents —CH$_2$—, —O—, —S— or —NR$^4$—, where R$^4$ is hydrogen or lower alkyl, whereas when ═ is a double bond, W represents ═CH—; G$^1$ and G$^2$ may be the same or different and each is hydrogen, lower alkyl, hydroxy or lower alkoxy; m is an integer of 1 through 3;

Y is —CH$_2$— or

l is an integer of 1 through 3;
R$^A$ is hydrogen, lower alkyl, lower alkanoyl, or substituted or unsubstituted aroyl;
R$^B$ is hydrogen;
Z is

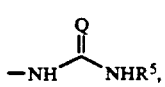

where Q is oxygen or sulfur, R$^5$ is hydrogen, lower alkyl, or substituted or unsubstituted aryl,

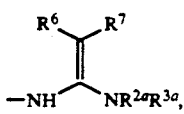

where R$^6$ and R$^7$ may be the same of different and each is hydrogen, cyano, lower alkoxycarbonyl, lower alkylsulfonyl, substituted or unsubstituted arylsulfonyl, or nitro; provided R$^6$ and R$^7$ cannot concurrently be hydrogen; R$^{2a}$ and R$^{3a}$ have the same meanings as R$^2$ and R$^3$ defined above.

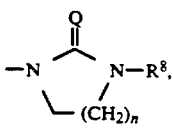

wherein n is 1 or 2; Q and R$^8$ are respectively as defined above,

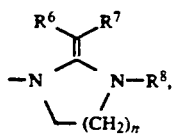

wherein $R^6$, $R^7$, $R^8$ and n are respectively as defined above,

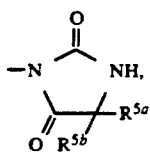

wherein $R^{5a}$ and $R^{5b}$ may be the same or different and each has the same meaning as $R^6$ defined above, or

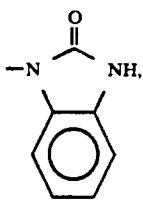

or a pharmaceutically acceptable salt thereof.

2. A compound of the formula:

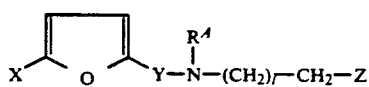

wherein X, Y, $R^4$, l and Z have the meanings given in claim 1.

3. The compound of claim 2, in which Y is $-CH_2-$, $R^4$ is hydrogen, lower alkyl and l is 1 or 2.

4. The compound of claim 3 in which Z is

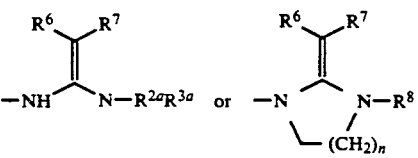

5. The compound of claim 4, in which X is

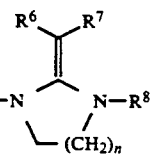

$R^4$ is hydrogen, l is 1 and Z is

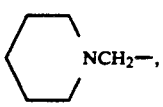

6. The compound of claim 4, in which X is $(CH_3)_2NCH_2-$, $R^4$ is hydrogen, l is 1 Z is

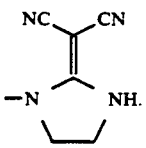

7. A pharmaceutical composition for the treatment of gastrointestinal disorders comprising an effective amount of the component of claim 1 together with a pharmaceutically acceptable carrier or diluent.

* * * * *